United States Patent [19]
Klein et al.

[11] Patent Number: 5,770,595
[45] Date of Patent: Jun. 23, 1998

[54] OXIME SUBSTITUTED THERAPEUTIC COMPOUNDS

[75] Inventors: J. Peter Klein, Vashon; Alistair Leigh, Brier, both of Wash.

[73] Assignee: Cell Therapeutics, Inc., Seattle, Wash.

[21] Appl. No.: 193,344

[22] Filed: Feb. 7, 1994

Related U.S. Application Data

[63] Continuation of Ser. No. 6,083, Jan. 19, 1993, abandoned.

[51] Int. Cl.$^6$ .................................................. M61K 31/52
[52] U.S. Cl. .......................... 514/263; 544/271; 544/273
[58] Field of Search ............................ 514/263; 544/271, 544/273

[56] References Cited

U.S. PATENT DOCUMENTS

| | | |
|---|---|---|
| 3,422,107 | 1/1969 | Mohler et al. . |
| 3,737,433 | 6/1973 | Mohler et al. . |
| 4,515,795 | 5/1985 | Hinze et al. . |
| 4,576,947 | 3/1986 | Hinze et al. . |
| 4,636,507 | 1/1987 | Kreutzer et al. . |
| 4,833,146 | 5/1989 | Gebert et al. . |
| 4,965,271 | 10/1990 | Mandell et al. . |
| 5,039,666 | 8/1991 | Novick et al. . |
| 5,096,906 | 3/1992 | Mandell et al. . |
| 5,112,827 | 5/1992 | Suander et al. . |
| 5,118,500 | 6/1992 | Hänel et al. . |
| 5,272,153 | 12/1993 | Mandell et al. . |
| 5,354,756 | 10/1994 | Underiner et al. ...................... 514/263 |
| 5,470,878 | 11/1995 | Michnick et al. ...................... 514/558 |
| 5,473,070 | 12/1995 | Underiner et al. ...................... 514/267 |
| 5,521,315 | 5/1996 | Underiner et al. ...................... 514/243 |
| B1 3,737,433 | 3/1987 | Mohler et al. . |

FOREIGN PATENT DOCUMENTS

| | | |
|---|---|---|
| A435152 | 7/1991 | European Pat. Off. . |
| A435153 | 7/1991 | European Pat. Off. . |
| 3942872 | 6/1991 | Germany . |

OTHER PUBLICATIONS

Chemical Abstract AN 115: 280052, Fraisse et al, EP 447324 A1, Sep. 18, 1991, Abstract Only.
Chemical Abstracts, AN 1969:37788, Zackowska et al, May 1969.
Chemical Abstracts, AN 1977:55392, Werner et al, Aug. 1976.
Chemical Abstracts, AN 1977:165145, Kokel et al, Nov. 1976.
CA 86:165145, Kokel et al, "Antiviral Properties of Theophylline Derivatives", *Eur. J. Med. Chem* vol. 11(6), pp. 527–532, 1976. Abstract Only.
CA 70:37788, Zajaczkowska et al, "The Search for New drugs in the Group of Xanthine Derivatives", *Diss. Pharm. Pharmacol.*, vol. 20(5), pp. 497–505, 1968. Abstract only.
Chem Abst 53: 11394(F) 1959.
Chem Abst. 70: 37788 1968.
Chem Abst. 51: 1204 (F) 1957.

Bianco et al., *Blood*, 76:Supplement 1 (522), p. 133a, "Pentoxifylline (PTX) and GM–CSF Decrease Tumor Necrosis Factor–ALPHA (TNF–α) Levels in Patients Undergoing Allogeneic Bone Marrow Transplantation (BMT)," 1991.
Davis et al., *Applied Environment Microbial.*, 48:2, pp. 327–331, "Microbial Models of Mammalian Metabolism: Microbial Reduction and Oxidation of Pentoxifylline," Aug. 1984.
Bursten et al., *The Journal of Biological Chemistry*, vol. 266, No. 31, pp. 20732–20743, "Interleukin–1 Rapidly Stimulates Lysophosphatidate Acyltransferase and Phosphatidate Phosphohydrolase Activities in Human Mesangial Cells", 1991.
Drabczynska et al., *Pol. J. Pharmacol. Pharm.*, vol. 28, pp. 95–103, "The Search for New Drugs in the Group of Xanthine Derivaties", 1976.
Epstein et al., *The New England Journal of Medicine*, vol. 328, No. 2, pp. 106–113, "The Role of Interleukin–1 in Disease", 1993.
Goodman et al., *Macmillan Publishing Company, Inc. (New York)*, pp. 1–46, "The Pharmacological Basis of Therapeutics", 1975.

*Primary Examiner*—Keith MacMillan
*Attorney, Agent, or Firm*—Stephen Faciszewski

[57] ABSTRACT

Oxime-substituted compounds are preferably cyclic or heterocyclic compounds. The oxime-substituted compounds and pharmaceutical compositions thereof have the formula:

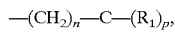

CORE MOIETY—(R)$_j$ including resolved enantiomers (both syn and anti forms) and/or diastereomers, hydrates, salts, solvates and mixtures thereof. j is an integer from one to three, the core moiety is non-cyclic or cyclic and R may be selected from among: hydrogen, halogen, hydroxyl, amino, substituted or unsubstituted $C_{(1-10)}$, alkyl, $C_{(2-10)}$ alkenyl, cyclic or heterocyclic groups, and formula I. At least one R has the formula I:

$$—(CH_2)_n—C—(R_1)_p, \qquad \text{I}$$

wherein n is an integer from three to twenty; p is two or three; $R_1$ is selected from among hydrogen; halogen; hydroxide; substituted or unsubstituted $C_{(1-10)}$ alkyl, $C_{(1-10)}$ alkoxy, $C_{(2-10)}$ alkenyl, cyclic or heterocyclic group; =N—OR$_2$, R$_2$ being hydrogen or a substitute or unsubstituted $C_{(1-10)}$ alkyl, $C_{(2-10)}$ alkenyl, cyclic or heterocyclic group; and —(CH$_2$)$_s$—C(R$_3$)$_t$ (wherein s is zero or an integer from one to ten, t is two or three, R$_3$ is hydrogen, halogen, hydroxide, substituted or unsubstituted $C_{(1-10)}$ alkyl, $C_{(1-10)}$ alkoxy, C$_{(2-10)}$ alkenyl, cyclic or heterocyclic group, or =N—OR$_2$, R$_2$ being defined above). At least one R$_1$ or one R$_3$ is =N—OR$_2$, p or t corresponding to the at least one R$_1$ or one R$_3$ is two, and a second R$_1$ or second R$_3$, bonded to the same —C as the at least one R$_1$ or one R$_3$, is other than =N—OR$_2$. These disclosed compounds are useful in a large variety of therapeutic indications for treating or preventing disease mediated by intracellular signaling through specific intracellular signaling pathways.

22 Claims, 19 Drawing Sheets

OXIME SUBSTITUTED THERAPEUTIC COMPOUNDS

CROSS REFERENCE TO RELATED APPLICATION

This is a Continuation-in-Part Application of U.S. application Ser. No. 08/006,083, filed Jan. 19, 1993.

TECHNICAL FIELD OF THE INVENTION

The invention relates to a class of oxime-substituted therapeutic compound that are effective agents to modulate cellular responses to stimuli. More specifically, the inventive compounds have at least one oxime-substituted side chain bonded to a core moiety. The inventive compounds are useful in a large variety of therapeutic indications for treating or preventing disease mediated by intracellular signaling through specific intracellular signaling pathways.

BACKGROUND ART

Pentoxifylline (1-(5-oxohexyl)-3,7-dimethylxanthine), abbreviated PTX, is xanthine derivative which has seen widespread medical use for the increase of blood flow. PTX is disclosed in U.S. Pat. Nos. 3,422,107 and 3,737,433, both to Mohler et al. Metabolites of PTX were summarized in Davis et al., *Applied Environment Microbiol.* 48:327, 1984. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947 to Hinze et al. In addition, U.S. Pat. Nos. 4,8.33,146 and 5,039,666 to Gebert et al. and Novick, Jr., respectively, disclose use of tertiary alcohol analogs of xanthine for enhancing cerebral blood flow.

Furthermore, U.S. Pat. No. 4,636,507 to Kreutzer et al. describes an ability of PTX and M1, to stimulate chemotaxis in polymorphonuclear leukocytes in response to a stimulator of chemotaxis. PTX and related tertiary alcohol substituted xanthines inhibit activity of certain cytokines to affect chemotaxis (U.S. Pat. Nos. 4,965,271 and 5,096,906 to Mandell et al.). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in assayable levels of TNF was accompanied by reduction in bone marrow transplant-related complications. However, in normal volunteers, TNF levels were higher among PTX recipients. Therefore, elevated levels of TNF are not the primary cause of such complications.

Therefore, there is a need in the art to discover effective therapeutic compounds that are safe and effective for human or animal administration and can maintain cellular homeostasis in the face of a variety of inflammatory stimuli. The present invention was made in a process of looking for such compounds.

SUMMARY OF THE INVENTION

The invention is directed to oxime-substituted therapeutic compounds. The inventive oxime-substituted compounds are useful in a large variety of therapeutic indications for treating or preventing disease. In particular, the inventive compounds and pharmaceutical compositions thereof provide therapy for diseases mediated by intracellular signaling through specific intracellular signaling pathways, more specifically, the pathway herein discussed.

The inventive compounds have at least one oxime-containing side chain and are preferably cyclic or heterocyclic compounds. The inventive compounds and pharmaceutical compositions thereof have the formula:

CORE MOIETY-(R)$_j$ including resolved enantiomers (both syn and anti forms) and/or diastereomers, hydrates, salts, solvates and mixtures thereof, wherein j is an integer from one to three, the core moiety is non-cyclic or cyclic and R may be selected from among: hydrogen, halogen (preferably bromine, chlorine, fluorine and iodine), hydroxyl, amino, substituted or unsubstituted $C_{(1-10)}$ alkyl, $C_{(2-10)}$ alkenyl, cyclic or heterocyclic groups, and groups having a structure prescribed by formula I, below.

Preferred R substituents having a structure other than prescribed by formula I below include, but are not limited to, methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, and the like. Particularly preferred R are ethyl, methyl, or hydrogen.

In the inventive compounds, at least one R has the formula I:

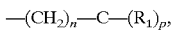

wherein n is an integer from three to twenty; p is two or three; $R_1$ is selected from among: hydrogen; halogen; hydroxide; substituted or unsubstituted $C_{(1-10)}$ alkyl, $C_{(1-10)}$ alkoxy, $C_{(2-10)}$ alkenyl, cyclic or heterocyclic group; =N—OR$_2$, R$_2$ being hydrogen or a substituted or unsubstituted $C_{(1-10)}$ alkyl, $C_{(2-10)}$ alkenyl, cyclic or heterocyclic group; —(CH$_2$)$_s$— C(R$_3$)$_t$ (wherein s is zero or an integer from one to ten, t is two or three, R$_3$ is hydrogen, halogen, hydroxide, substituted or unsubstituted $C_{(1-10)}$ alkyl, $C_{(1-10)}$ alkoxy, $C_{(2-10)}$ alkenyl, cyclic or heterocyclic group, or =N—OR$_2$, R$_2$ being defined above); and at least one s R$_1$ or one R$_3$ is =N—OR$_2$, p or t corresponding to the at least one R$_1$ or one R$_3$ is two, and a second R$_1$ or second R$_3$, bonded to the same —C as the at least one R$_1$ or one R$_3$, is other than =N—OR$_2$. Optionally, (CH$_2$)$_n$ and/or (CH$_2$)$_s$ may have one or two unsaturated bonds (preferably in a cis configuration) or be interrupted by at least one oxygen atom.

A non-cyclic core moiety may include, but is not limited to, for example, acetamide, amide, amine, amino acid (one or two), carboxide, ester, terminal halogen or hydrogen atom, hydroxide, glutaric acid, glycine derivative, ketone, phosphate, phosphonate, sulfate, sulfonate, sulfone, sulfoxide, simple ionic functional group, thiol or thiolester. Exemplary core moiety amino acids may include one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

A cyclic core may be at least one five- to seven-member non-heterocyclic ring or a heterocycle. The at least one five- to seven-membered non-heterocyclic ring may preferably have from one to three, five- to six-membered ring structures in a predominantly planar configuration. For example, the core moiety may be selected from the group consisting of substituted or unsubstituted benzene; biphenyl; cyclohexane; cyclohexanedione; cyclopentanedione; napthlalene; phenol; salicylic acid and derivatives thereof; stilbene or tricyclododecane.

Although other heterocyclic cores are within the scope of the invention, the following cores are representative heterocyclic cores: substituted or unsubstituted barbituric acid;

benzamide; lactam; glutarimide; homophthalimide; hydrophthalimide; imidazole; imidazole amide; indomethacin; isocarbostyril; lumazine; N-alkylheterocyclic; N-heterocyclic; pteridine; pthalimide; piperidine; pyridine; pyrimidine; pyrrole amide; quaternized N-heterocyclic; quinolizinedione; quinazolinone; quinolone; recorsinol; succinimide; theobromine; thymine; triazine; uric acid; uracil; vitamins A, E or K; or xanthine.

Preferably, R is bonded to a nitrogen of the core moiety, most preferably the core moiety is xanthine and R of formula I is bonded to an $N_1$ xanthine nitrogen and $N_3$ and $N_7$ xanthine nitrogens are independently substituted by a member selected from the group consisting of hydrogen, methyl, fluoro, chloro and amino. Representative, preferred inventive compounds are compounds of formula II:

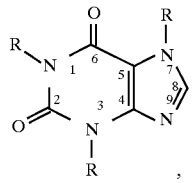

II wherein R is defined above. A single R of formula I above may be bonded to the $N_1$ xanthine nitrogen or each of two R of formula I may be bonded to $N_1$ and $N_7$ xanthine nitrogens, respectively, in a covalent bond, or by an ether, ester, or peptide linkage.

The present invention further provides pharmaceutical compositions suitable for normal routes of therapeutic administration, providing effective compound dosages. The inventive pharmaceutical compositions comprise inventive compound and a pharmaceutically acceptable excipient or carrier, formulated for, e.g., parenteral, oral, topical and other known methods of pharmaceutical administration.

The invention includes a method for treating an individual having a variety of diseases. The disease is characterized by or can be treated by inhibiting an immune response or a cellular response to external or in situ primary stimuli, the cellular response being mediated through a specific phospholipid-based second messenger pathway described herein. The second messenger pathway is activated in response to various noxious, proinflammatory or proliferative stimuli characteristic of a variety of disease states. More specifically, the invention includes methods for treating or preventing clinical symptoms of various disease states or reducing toxicity of other treatments by inhibiting cellular signaling through a second messenger pathway involving signaling through a non-arachidonyl phosphatidic acid intermediate.

A disease state or treatment-induced toxicity are selected from the group consisting of: tumor progression involving tumor stimulation of blood supply (angiogenesis) by production of fibroblast growth factor (FGF), vascular endothelial growth factor (VEGF) or platelet-derived growth factor (PDGF); tumor invasion and formation of metastases through adhesion molecule binding, expressed by vascular endothelial cells (VCAM and ICAM); tissue invasion through tumor metalloprotease production such as MMP-9; autoimmune diseases caused by dysregulation of the T cell or B cell immune systems, treatable by suppression of the T cell or B cell responses; acute allergic reactions including, but not limited to, asthma and chronic inflammatory diseases, mediated by proinflammatory cytokines including tumor necrosis factor (TNF) and IL-1; rheumatoid arthritis, osteoarthritis, multiple sclerosis or insulin dependent diabetes mellitus (IDDM), associated with enhanced localization of inflammatory cells and release of inflammatory cytokines and metalloproteases; smooth muscle cell, endothelial cell, fibroblast and other cell type proliferation in response to growth factors, such as PDGF-AA, BB, FGF, EGF, etc. (i.e., atherosclerosis, restenosis, stroke, and coronary artery disease); activation of human immunodeficiency virus infection (AIDS and AIDS related complex); HIV-associated dementia; kidney mesengial cell proliferation in response to IL-1, MIP-1α, PDGF or FGF; kidney glomerular or tubular toxicity in response to cyclosporin A or amphotericin B treatment; organ toxicity (e.g., gastrointestinal or pulmonary epithelial) in response to a cytotoxic therapy (e.g., cytotoxic drug or radiation); effects of non-alkylating anti-tumor agents; inflammation, particularly in response to inflammatory stimuli (e.g., TNF, IL-1 and the like), characterized by production of metalloproteases or allergies due to degranulation of mast cells and basophils in response to IgE or RANTES; bone diseases caused by overproduction of osteoclast-activating factor (OAF) by osteoclasts; central nervous system diseases resulting from over-stimulation by proinflammatory neurotransmitters such as, acetylcholine, serotonin, leuenkephalin or glutamate; acute inflammatory diseases such as septic shock and adult respiratory distress syndrome; multi-organ dysfunction associated with inflammatory cytokine cascade and combinations thereof.

In many cell types, signaling is dependent upon generation of a broad variety of non-arachidonyl PA species, some of which are generated from lyso-PA by the enzyme lyso-PA acyl transferase (LPAAT). Generation of each of these PA species (the predominant forms being: 1-acyl, and 1-alkyl, 2-linoleoyl PA compounds, generated by LPAAT) serves to effect both proliferative and/or inflammatory signaling in the diseases discussed and cell signaling systems described above.

The inventive compounds are of particular significance for inhibiting IL-2-induced, proliferative response. IL-2 signaling inhibition is potentially useful in the treatment of numerous disease states involving T-cell activation and hyperproliferation. Exemplary, important autoimmune diseases are lupus, scleroderma, rheumatoid arthritis, multiple sclerosis, glomerula nephritis, insulin dependent diabetes mellitus (IDDM), as well as potential malignancies, including but not limited to, chronic myelogenous leukemia as well as others.

BRIEF DESCRIPTION OF THE DRAWINGS

FIG. 6 reports that compound no. 1521 inhibited TNF release.

FIG. 7 illustrates inhibition of TNF release in this investigation by compound no. 1521.

FIG. 11 is a plot of mean fluorescence intensity of cells analyzed by flow cytometry for compounds nos. 1521 and 1522, at the indicated drug concentrations.

FIG. 12 shows that both inventive compounds were active in this predictive in vitro model.

As shown in FIG. 13, this inventive compound tested was essentially not toxic at therapeutic concentrations to cells tested.

DETAILED DESCRIPTION OF THE INVENTION

Figure 1:
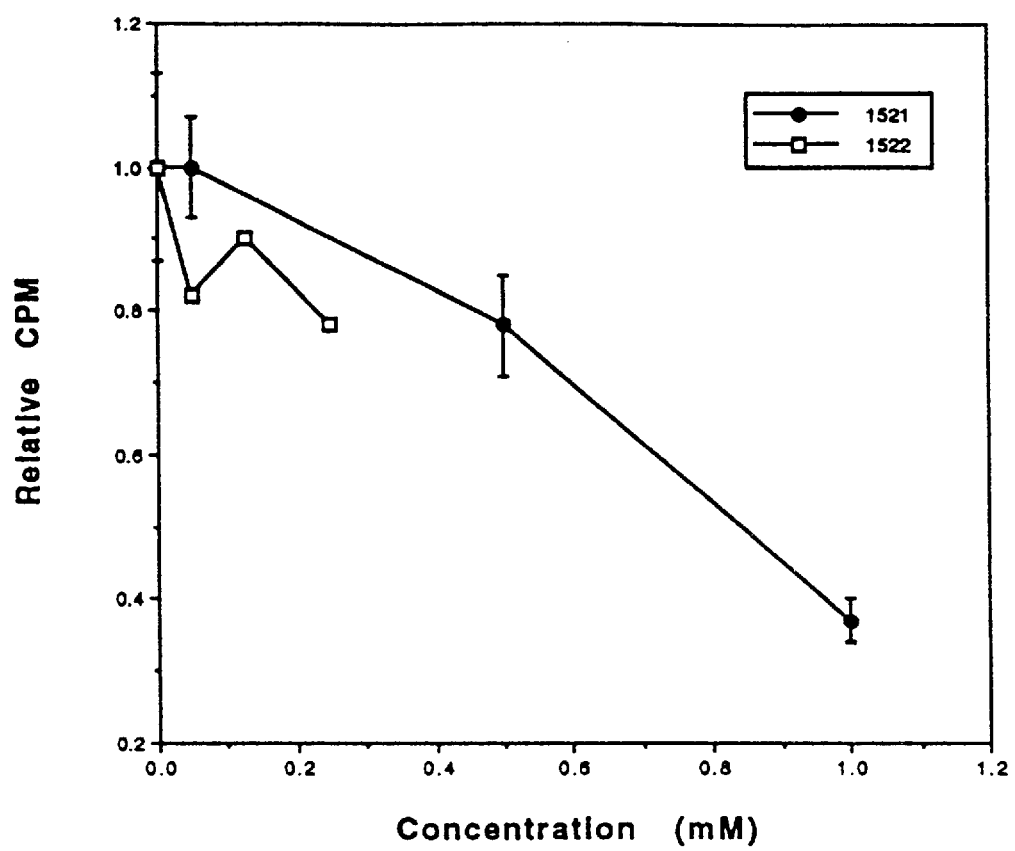
FIG. 1 shows a mixed lymphocyte reaction of inventive compounds nos. 1521 and 1522 (see below for chemical name and structure). The mixed lymphocyte reaction shows a proliferative response of PBMC (peripheral blood mononuclear cells) to allogeneic stimulation determined in a two-way mixed lymphocyte reaction.

The invention provides a genus of compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine
LPE=lysophosphoethanolamine
PA=phosphatidic acid
LPA=lysophosphatidic acid
DAG=diacylglycerol
LPLD=lysophospholipase-D
LPAAT=lysophosphatidic acid acyl transferase
PAPH=phosphatidic acid phosphohydrolase
PLA2=phospholipase A2.
PLD=phospholipase D
PAA=phosphoarachidonic acid
PC=phosphatidyl choline "remodeled" PA, cyclic pathway=PAA, LPA, PA and DAG intermediate substituted with 1-saturated, 2-linoleoyl or 1,2-dioleoyl, dioleoyl/1,2-sn-dilinoleoyl at the indicated sn-i and sn-2 positions.

"Classical PI Pathway"=PI, DAG, PA intermediates substituted with 1-stearoyl, 2-arachidonoyl fatty acyl side chains.

"PLD-generated PA"=PE, PC, LPA, PA and DAG intermediates substituted with, e.g., 1,2-sn-dioleoyl-, 1-alkyl, 2-linoleoyl-, and 1-alkyl, 2-docosahexaenoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. Administration of the compounds of the invention reverse this elevation.

The compounds and pharmaceutical compositions of the invention include inhibitors of subspecies of LPAAT and PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2-diunsaturated and 1-alkyl, 2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

Each membrane phospholipid subclass (e.g., PA, PI, PE, PC and PS) reaches a stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmitate. In resting cells, PC's acyl side chains consist mostly of acyl palmitate in the sn-i position and oleate in the sn-2 position. PE and PI are predominantly composed of sn-I stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. It is important to know whether or not each phospholipid species passes through a PA form prior to hydrolysis to DAG. The lyso-PA that is converted to PA and then to DAG may be shown. The complexities of this second messenger pathway can be sorted by suitable analyses using fatty acyl side chain chemistry (e.g., by thin layer chromatography, gas-liquid chromatography, or high pressure liquid chromatography) of intermediates in cells at various time points after stimulation of the second messenger pathway.

In certain meseachymal cells, such as neutrophils and rat or human mesangial cells, several signaling pathways may be activated in tandem, simultaneously or both. For example, in neutrophils, F-Met-Leu-Phe stimulates formation of PA through the action of PLD, followed in time by formation of DAG through PAPH action. Several minutes later, DAG is generated from PI through the classical phosphoinositide pathway. In many cells, DAG is derived from both PA that is remodeled through a cycle whereby PA is sn-2 hydrolyzed by PLA2, followed by sn-2 transacylation by LPAAT and PA that is generated in a PLD-pathway from either PE or PC or both substrates by PLD.

The present second messenger pathway involves substrates with unsaturated fatty acids in the sn-2 position other than arachidonate and those sub-species of PAPH and LPAAT that are not involved in normal cellular housekeeping functions that are part of the classical PI pathway. The PAPH and LPAAT enzymes involved in this specific second messenger pathway are exquisitely stereo-specific for different acyl side chains and isomeric forms of substrates. Therefore, the inventive compounds may preferably be substantially enantiomerically pure.

PTX (in vitro) blocks formation of remodeled PA through the PA/DAG pathway at high PTX concentrations (greater than those that could be achieved in patients without dose-limiting side effects) by blocking formation of PA subspecies at LPAAT. Even in the presence of PTX, cells continue to form PA through the action of PLD, and DAG is also formed through the action of phospholipase C on PC and PI. The latter pathway are not inhibited by the inventive compounds or PTX. In PTX-treated cells, DAG derived from remodeled and PLA-generated PA is diminished (e.g., 1,2-sn-dioleoyl DAG, 1-alkyl, 2-linoleoyl DAG and 1-alkyl, 2-docosahexaneolyl DAG). Therefore, the inventive compounds and PTX inhibit the formation of only a certain species of PA and DAG by selectively inhibiting a specific second messenger pathway that is only activated in cells by noxious stimuli, but is not used to signal normal cellular housekeeping functions.

Therapeutic Uses of the Inventive Compounds

The specific activation inhibition of the second messenger pathway, as described above and activated primarily by various noxious stimuli, suggests that the inventive compounds are useful in treating a wide variety of clinical indications, mediated a the cellular level by a common mechanism of action. Moreover, in vitro and in vivo data presented herein provides predictive data that a wide variety of clinical indications, having similar effects on the specific second messenger pathway (activated by noxious stimuli and mediated through, for example, inflammatory cytokines), may be treated by the inventive compounds, which specifically inhibit the pathway. In fact, the mechanism of action for the inventive compounds explains why these compounds have multifarious clinical indications.

Activation of the second messenger pathway is a major mediator of response to noxious stimuli and results in cellular signals that lead to, for example, acute and chronic inflammation, immune response and cancer cell growth. Although the inventive compounds may desirably inhibit other noxious stimuli not discussed, they most effectively mediate the above conditions. Signals mediated by the present second messenger pathway include, for example, those cellular responses of LPS directly; T cell activation by antigen; B cell activation by antigen, cellular responses to IL-1, mediated through the IL-1 Type I receptor (but not the IL-1 Type II receptor), and TNF (Type I receptor), growth stimulated by transformations including, but not limited to, activated oncogenes (e.g., ras, abl, her 2-neu and the like), smooth muscle cell proliferation stimulated by PDGF, b-FGF and IL-1; T cell and B cell growth stimulation by IL-2, IL-4 or IL-7 and IL-4 or IL-6, respectively; and more generally, T cell receptor signaling.

In vitro, the inventive compounds: (1) block IL-1 signal transduction through the Type 1 receptor as shown, for example, by preventing IL-1 and IL-1 plus PDGF (platelet derived growth factor) induction of proliferation of smooth muscle, endothelial and kidney mesengial cells; (2) suppress up-regulation of adhesion molecules as shown, for example, by blocking VCAM in endothelial cells; (3) inhibit TNF, LPS and IL-1 induced metalloproteases (an inflammation model); (4) block LPS, TNF or IL-1 induced metalloprotease and secondary cytokine production (for prevention and treatment of septic shock); (5) suppress T cell and B cell activation by antigen, for example, IL-2 and IL-4; (6) inhibit mast cell activation by IgE; (7) are cytotoxic for transformed cells and tumor cell lines, yet not for normal cells; and (8) block signaling by IL-2, IL4, IL-6 and IL-7I on T and B cells.

The foregoing in vitro effects give rise to the following in vivo biological effects, including, but not limited to: protection and treatment of endotoxic shock and sepsis induced by gram positive or gram negative bacteria; inhibition of tumor cell growth; synergistic immunosuppression, active in autoimmune diseases and in suppressing allograft reactions; and stimulation of hair grow through reversal of an apoptotic process. The inventive compounds are most potent when used to prevent and treat septic shock, treat acute and chronic inflammatory disease, treat or prevent an autoimmune disease and stimulate hair growth (when applied topically).

The inventive compounds also are useful as an adjuvant to inhibit toxic side effects of drugs whose side effects are mediated through the present second messenger pathway.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus bFGF, a 72 kD type IV collagenase that is usually constitutive and induced by TNF or IL-1, and a stromelysin/PUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. Accordingly, the inventive compounds prevent induction of certain metalloproteases induced by IL-1 or TNF and are not involved with constitutively produced proteases (e.g., 72 kD type IV collagenase) involved in normal tissue remodeling.

The inventive compounds inhibit signal transduction mediated through the Type I IL-1 receptor, and are therefore considered as IL-1 antagonists. A recent review article entitled "The Role of Interleukin-1 in Disease" (Dinarello et al., *N. Engl. J. Med.* 328, 106, Jan. 14, 1993) described the role of IL-1 as "an important rapid and direct determinant of disease . . . . In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue." The article describes a group of diseases that are mediated by IL-1, including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above-mentioned diseases.

For example, for sepsis syndrome, the mechanism of IL-i-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure and doses of 300 ng or more per kilogram of body weight may cause severe hypotension. The therapeutic advantage of blocking the action of IL-1 resides in preventing its deleterious biological effects without interfering with the production of molecules that have a role in homeostasis. The present inventive compounds address this need, identified by Dinarello et al., by inhibiting cellular signaling only through the IL-1 Type I receptor and not through the IL-1 Type II receptor.

With regard to rheumatoid arthritis, Dinarello and Wolff state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ ($PGE_2$), leukotriene $B_4$ ($LTB_4$) and IL-8, an inflammatory cytokine with neutrophil-chemoattractant and neutrophil-stimulating properties. Tissue concentrations of PGE2 and LTB4 correlate to severity of disease in patients with ulcerative colitis, patients with inflammatory bowel disease having high tissue concentrations of IL-1 and IL-8. Therefore, an IL-1 antagonist, such as the inventive compounds, would be effective to treat inflammatory bowel disease.

With regard to acute and chronic myelogenous leukemia, there is increasing evidence that IL-1 acts as a growth factor for such tumor cells. Therefore, the inventive compounds should be effective to prevent the growth of worsening of disease for acute and chronic myelogenous leukemias.

Insulin-dependent diabetes mellitus (IDDM) is considered to be an autoimmune disease with destruction of beta cells in the islets of Langerhans, mediated by immunocompetent cells. Islets of animals with spontaneously occurring IDDM (e.g., BB rats or NOD mice) have inflammatory cells that contain IL-1. Therefore, the inventive compounds should be useful for the preventing and treating IDDM.

IL-1 also plays a role in atherosclerosis development. Endothelial cells are a target of IL-1. IL-1 stimulates proliferation of vascular smooth muscle cells. Foam cells, isolated from fatty arterial plaques from hypercholesterolemic rabbits, contain IL-1β and IL-1β messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds should be useful in preventing and treating atherosclerosis.

IL-1 activates (through the Type I IL-1 receptor) a lyso-PA acyltransferase (LPAAT) and phosphatidate phosphohydrolase within 5 seconds of cell (for example, human mesangial cells, HMC) exposure to this cytokine. As discussed in detail above, activation of both enzymes results in production of PA species with sn-1 and sn-2 unsaturated acyl groups, with the majority of sn-2 acyl chains being polyunsaturated. Both IL-1 and a product of LPAAT, 1,2-sn-dilinoleoyl PA, activate a signaling pathway involving hydrolysis of PE to PA. This reaction is followed by dephosphorylation of PA to produce both 1,2-sn-diacylglycerol, and 1-o-alkyl, or 1-o-alkenyl,acylglycerol (AAG) species. The inventive compounds exert their activity by inhibiting one or both enzymes at an inner leaflet of the plasma membrane. Therefore, appropriate in vitro models for drug activity may measure inhibition of stimulation caused by a proinflammatory cytokine or other inflammatory cellular signal.

The generation of the sn-2 unsaturated PA fraction by LPAAT serves to activate either G-proteins, or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of di-unsaturated PA, which is less than about 0.1% of total membrane lipid mass, is sufficient to activate PLD activity. This quantity of PA is similar to that endogeneously synthesized by LPAAT.

The PA-stimulated PLD acts upon PE, which should be localized to the inner leaflet of the cell membrane, enriched in PE relative to the outer leaflet. Therefore, the cellular inflammatory response to IL-1 is mediated by the pathway: IL-1R→PA→(PLD)→PE. Whereas a localized tissue response is: lysoPA→PI→PKC →(PLD)→PC. The PLD species are likely to be different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e., >30 minutes) is maintained by PC-derived PA generated by PC-directed PLD. Therefore, the pathway inhibited by the inventive compounds is PE-directed and not PC-directed. Moreover, the PE-directed PLD favors substrates with sn-2 long-chain unsaturation.

DAG and PA are upregulated in oncogenically transformed cells. For example, activating ras mutations result in increased generation of DAG upon stimulation with mitogens, although the sources of DAG differ between experimental systems. In nontransformed renal mesangial cells, IL-1β stimulation increased PLA2 and LPAAT activation, resulting in generation of sn-2 unsaturated PA and subsequent hydrolysis to DAG by phosphatidate phosphohydrolase. The ras transformation in NIH/3T3 cells upregulates serum-stimulated generation of DAG and PA. Particular species of DAG that is stimulated by serum is dioleoyl and of PA are dilinoleoyl and dioleoyl. This upregulation occurs over 4–12 hours and pretreatment of cells with an inventive compound, or PTX, blocks generation of these phospholipid second messengers. The inhibition occurs either through suppressing the generation of PA de novo from lysoPA, or through inhibition of one or both arms of the Lands cycle. The coordinate increase of lysoPA in the setting of diminished PA/DAG production suggests inhibition of transacylation of a precursor lipid. Therefore, the ras transformation mediates an upregulation of PA through indirect stimulation of PLA2 and/or LPAAT activity. The inventive compounds inhibit the conversion of the upregulated lysoPA to PA and subsequently block the phenotypic, changes induced by PA/DAG in the membrane.

The ability of the inventive compounds to inhibit generation of unsaturated phospholipids is mirrored by the ability of inventive compounds to inhibit proliferation and tumorogenicity of ras-transformed cells in vitro and in vivo. PTX inhibits ras-transformed NIH/3T3 cells more than parental cells. This inhibition is reversible and is not associated with significant cytotoxicity.

Excessive or unregulated TNF (tumor necrosis factor) production is implicated in mediating or exacerbating a number of diseases including rheumatoid arthritis rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, AIDS, other viral infections (e.g., CMV, influenza, adenovirus, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled through the present second messenger cellular phospholipid-based signaling pathway and by excessive or unregulated production of "first messenger" inflammatory cytokines such as TNF or IL-1. With regard to TNF first messenger signaling, there are several disease states in which excessive or unregulated TNF production by monocytes/macrophages is implicated in exacerbating or causing the disease. These include, for example, neurodegenerative diseases such as Alzheimers disease, endotoxemia or toxic shock syndrome (Tracey et al., Nature 330:662, 1987 and Hinshaw et al., Circ. Shock 30:279, 1990); cachexia (Dezube et al., Lancet 355:662, 1990), and adult respiratory distress syndrome (Miller et al., Lancet 2(8665):712, 1989). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., N. Engl. J. Med. 320:1585, 1989), chronic pulmonary inflammatory diseases such as silicosis and asbestosis (Piguet et al., Nature 344:245, 1990, and Bissonnette et al., Inflammation 13:329, 1989), and reperfusion injury (Vedder et al., Proc. Natl. Acad. Sci. USA 87:2643, 1990).

The compounds of the invention can inhibit certain VEGF (vascular endothelial growth factor), FGF (fibroblast growth factor) and PDGF (platelet derived growth factor) effects in vivo, such as inhibition of angiogenesis or restenosis. For example, Ferns et al., Science 253:1129, 1991, have shown that neointimal smooth muscle chemotaxis and angioplasty are inhibited in rats using a neutralizing antibody to PDGF. Also, Jawien et al., J. Clin Invest. 89:507, 1992, have shown that PDGF promotes smooth muscle migration and intimal thickening in a rat model of balloon angioplasty. Inhibition of the PDGF-mediated effects following balloon angioplasty by the inventive compounds is the pharmacological rationale for using the inventive compounds as therapeutic agents to prevent restenosis. The inventive compounds also inhibit atherogenesis because increased levels of PDGF expressed by macrophages are associated with all phases of atherogenesis (Ross et al., Science 248:1009, 1990). Further, many human tumors express elevated levels of either PDGF, FGF, receptors for FGF or PDGF, or mutated cellular oncogenes highly homologous to these growth factors or their receptors. For example, such tumor cell lines include sarcoma cell lines (Leveen et al., Int. J. Cancer 46:1066, 1990), metastatic melanoma cells (Yamanishi et al., Cancer Res. 52:5024, 1992), and glial tumors (Fleming et al., Cancer Res. 52:4550, 1992).

The inventive compounds are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

In Vitro Assays for Physiologic and Pharmacologic Effects of the Inventive Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min at 37° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 $\mu l$ complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate. The cultures are incubated for 6 days at 37° C. in a 5% $CO_2$ atmosphere. At the conclusion of the incubation tritiated thymidine is added (for example, 1 $\mu Ci$/well of 40 to 60 Ci/mmole) and proliferation determined by liquid scintillation. counting.

A thymocyte costimulator assay is conducted to evaluate the inventive compounds to inhibit activation and proliferation of thymocytes caused by stimulation with Con A and interleukin-1 (IL-1), or interleukin-1 (IL-2). Thymuses are obtained from mice (e.g., female Balb/C mice) and the thymuses are removed and dissociated into culture media (e.g., RPMI 1640 without serum supplementation). The dissociated thymus tissue and cell suspension is transferred to centrifuge tubes and allowed to settle, washed with HBSS and resuspended in serum-supplemented culture media (e.g., RPMI 1640 with 10% fetal calf serum). Any contaminating red cells are lysed, and viable cells are resuspended and counted. Thymocytes are plated (e.g., 96-well plates at a density of $2\times10^5$ cells/well) and a stimulating agent, such as Con A, IL-1 (e.g., IL-1$\alpha$) or IL-2 is added to the well. The cells are incubated for 4 days at 37° C. On the fourth day, the cells are pulsed with tritiated thymidine and cell proliferation determined. Inventive compounds are added at the time of stimulating agent addition.

Each inventive compound is investigated for cytotoxicity to determine appropriate doses for biological activity assays and to prevent cytotoxic reactions in in vitro assays when characterizing activity. Cells (e.g., NIH-3T3, Ras transformed 3T3 cells, malignant melanoma LD2 cells, etc.) are added to microtiter plates and drug is added about two days after plating. Cell viability is determined using a fluorescent viability slain (e.g., 2',7'-bis-(2-carboroxyethyl)-5-(and -6)-carboxyfluorescein acetoxymethyl ester, BCECF excitation 488 nm and emission 525 nm) 24, 48 or 72 hours after addition of the drug.

Another assay for measuring activity of the inventive compounds involves determining PDGF (platelet derived growth factor) proliferative response using human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1$\alpha$ or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 $\mu g$/ml), IL-4 or PMA (2.5 nM). Ramos B-cell tumor cells or murine splenocytes can be incubated with a stimulating agent, an inventive compound and tritiated thymidine to measure inhibition of cell proliferation caused by the stimulating agent.

Drug inhibitory activity can also be measured by determining levels of vascular cell adhesion molecule (VCAM) in stimulated cells. Early passage human umbilical vein endothelial cells (HUVEC) (obtained from commercial suppliers such as Cell Systems, Inc. or Clonetics) are cultured in media (e.g., Hepes buffered media, Cell Systems) containing 10% fetal bovine serum, and supplemented with a stimulating agent, such as fibroblast growth factor (acidic FGF, Cell Systems, Inc.) or TNF. The cells are plated into wells of a microtiter plate (e.g., $5\times10^4$ per well) and allowed to incubate at 37° C. for 72 hrs. The resting cells are removed (e.g., 20–30 min treatment with 0.4% EDTA), washed in media (e.g., phosphate buffered saline plus 0.1% bovine serum albumin with 0.01% sodium azide) and labeled on ice with a monoclonal antibody ("first antibody") recognizing human VCAM (e.g., 1 $\mu g$ of a murine monoclonal antibody recognizing human VCAM, Genzyme). After 60 min on ice, the cells are washed (preferably twice) with cold wash media and incubated with an antibody that recognizes the first antibody (e.g., 1 $\mu g$ of goat anti-mouse IgG conjugated with phycoerythrin, CalTag, Inc.). After 30 min on ice, the cells are washed twice and analyzed on a flow cytometer (Coulter Elite®) at appropriate emission and excitation wavelengths (e.g., for phycoerytlrin use excitation at 488 nm and emission at 525 nm).

One in vitro assay measures inhibition of the relevant enzymes lysophosphatidic acid acyltransferase (LPAAT) and phosphatidic acid phosphoryl hydrolase (PAPH). The assay involves incubating of target cells with a primary stimulus (e.g., a variety of cytokines, growth factors, oncogene products, putative therapeutic agents, irradiation, viral infection, toxins, bacterial infection and the products thereof, and any stimulus which, if not counteracted, has a deleterious effect on the target cell) in the presence or absence of an inventive compound at varying dosage levels. Target cells include, for example, subcellular entities, such as, microsomes derived from mesenchymal and/or ectodermal cells, particularly microsomes from marrow stromal cells or human or rat mesangial cells; microsomes or synaptosomes derived from bovine brain; plasma membrane-enriched microsomes, plasma membranes derived as described in Bursten et al. (J. Biol. Chem. 226:20732–20743, 1991), or detergent-solubilized microsomes; synaptosomes, and membranes or other cell preparations solubilized using, for example, NP40, Miranal, SDS or other neutral detergents; and detergent-solubilized, recombinant, or further purified preparations of cell proteins, including the proteins LPAAT and/or PAPH. After incubation for short periods of time, cell lipids are extracted and assayed by thin layer chromatography according to standard procedures. Briefly, lipids are extracted using, for example, chloroform:methanol 2:1 (v/v), and the extracts are then subjected to HPLC as described in Bursten and Harris, Biochemistry 30:6195–6203, 1991. A Rainin® mu-Porasil column is used with a 3:4 hexane:propanol organic carrier and a 1–10% water gradient during the first 10 minutes of separation. Detection of the peaks in the elution pattern is by absorption in the range of ultraviolet which detects isolated double bonds. The relevant peaks of unsaturated PA and DAG are shown in the elution pattern. It is important to note that the assay method permits discrimination between various forms of PA and DAG so that those relevant to the pathway affected by the (R) or (S) compounds of the invention can be measured directly. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5–60 seconds after stimulation with the primary stimulus, such as a cytokine. This technique permits assessment of the levels of various lipid components as a function of time.

An inventive compound can be assayed for activity protecting TNF-mediated cytotoxicity. In this assay, L929 murine fibroblast cells ($10^4$ cells per well) are incubated with either compounds at varying doses and media control for two hrs. TNF-α (R&D Systems) is added at a concentration of 500 pg/ml, which is four times the LD50 of TNF (125 pg/ml). The cells plus (or minus) drug plus TNF were incubated for 40 hrs at 37° C. The media is removed and replaced with fresh media containing 2% serum and 10 μg/ml of BCECF fluorescent dye and incubated for 30 min. The fluorescent dye-containing media is removed and replaced with PBS (phosphate buffered saline) and each well was assayed for fluorescence.

Another assay measures the effects of drug to inhibit adhesion of U937 cells to TNF-activated HUVEC cells In this experiment, HUVEC cells are induced with human TNF-α (20 ng/ml) and drug at varying concentrations for 14–16 hrs. U937 cells (a human monocyte cell line) are incubated and labeled with BCECF (10 μg/ml), a fluorescent dye. The U937 cell preparation ($2.5 \times 10^4$ cells per well) is layered on top of the activated HUVEC cells. The cells are reverse spun to remove partially adhering and nonadhering U937 cell. The adherent U937 cells are measured by fluorescence on a fluorescent plate reader.

Compounds of the Invention

The invention is directed to oxime-substituted therapeutic compounds and uses thereof. The inventive oxime-substituted compounds are useful in a large variety of therapeutic indications for treating or preventing disease. In particular, the inventive compounds and pharmaceutical compositions thereof provide therapy for diseases mediated by intracellular signaling through specific intracellular signaling pathways, more specifically, the pathways herein discussed.

The inventive compounds have at least one oxime-containing side chain and are preferably cyclic or heterocyclic compounds. The inventive compounds and pharmaceutical compositions thereof have the formula:

CORE MOIETY-(R)$_j$ including resolved enantiomers (both syn and anti forms) and/or diastereomers, hydrates, salts, solvates and mixtures thereof, wherein j is an integer from one to three, the core moiety is non-cyclic or cyclic and R may be selected from among: hydrogen, halogen (preferably bromine, chlorine, fluorine and iodine), hydroxyl, amino, substituted or unsubstituted $C_{(1-10)}$ alkyl, $C_{(2-10)}$ alkenyl, cyclic or heterocyclic groups, and groups having a structure prescribed by formula I, below.

Preferred R substituents having a structure other than prescribed by formula I below include, but are not limited to, methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, and the like. Particularly preferred R are ethyl, methyl, or hydrogen.

In the inventive compounds, at least one R has the formula I:

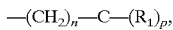

$$—(CH_2)_n—C—(R_1)_p, \qquad I$$

wherein n is an integer from three to twenty; p is two or three; $R_1$ is selected from among: hydrogen; halogen; hydroxide; substituted or unsubstituted $C_{(1-10)}$ alkyl, $C_{(1-10)}$ alkoxy, $C_{(2-10)}$ alkenyl, cyclic or heterocyclic group; =N—OR$_2$, $R_2$ being hydrogen or a substituted or unsubstituted $C_{(1-10)}$ alkyl, $C_{(2-10)}$ alkenyl, cyclic or heterocyclic group; —(CH$_2$)$_1$— C(R$_3$)$_t$ (wherein s is zero or an integer from one to ten, t is two or three, R$_3$ is hydrogen, halogen, hydroxide, substituted or unsubstituted C$_{(10)}$ alkyl, C$_{(1-10)}$ alkoxy, C$_{(2-10)}$alkenyl, cyclic or heterocyclic group, or =N—OR$_2$, R$_2$ being defined above); and at least one R$_1$ or one R$_3$ is =N—OR$_2$, p or t corresponding to the at least one R$_1$ or one R$_3$ is two, and a second R$_1$ or second R$_3$, bonded to the same —C as the at least one R$_1$ or one R$_3$, is other than =N—OR$_2$. Optionally, (CH$_2$)$_n$ and/or (CH$_2$)$_s$ may have one or two unsaturated bonds (preferably in a cis configuration) or be interrupted by at least one oxygen atom.

Preferably, n is an integer from about three to about eighteen, more preferably, an integer from about three to about seven. In especially preferred compounds, p is two, one R$_1$ of —C(R$_1$)$_2$ is =N—OR$_2$, R$_2$ being preferably hydrogen or C$_{(1-10)}$ alkyl, and the second R$_1$ is a C$_{(1-10)}$ alkyl (preferably methyl) or C$_{(1-10)}$ alkoxy.

Although other possible substituents are within the scope of the inventive compounds, representative substituents for any of R/R$_1$/R$_2$/R$_3$ substituted C$_{(1-10)}$ alkyl, C$_{(1-10)}$ alkoxy, C$_{(2-10)}$ alkenyl, cyclic or heterocyclic groups may be selected from among amide, primary, secondary and tertiary amine, C$_{(2-8)}$ alkenyl, C$_{(1-8)}$ alkyl (including, e.g., branched and unbranched alkyl or alkenyl groups), C$_{(1-8)}$ alkoxy, azide, carbonate, carbonyl, carboxylic acid, cyanide, C$_{(1-8)}$ haloalkyl (including, e.g., mono-, di- and tri-haloalkyl substituents, such as trihalomethyl), isocyanate, isothiocyanate, phosphate, phosphonate, primary, secondary or tertiary alcohol (including, e.g., any one of various diols, methanol, butanol, 1-cyclopentanol, ethanol, 2-ethyl-3-methyl-1-propanol, pentanol, propanol, and methylcyclohexanol), sulfonate, sulfone, sulfoxide, thioamide, thiocarbonate thioester, thiolester, thiol, thiourea and urea.

Representative R/R$_1$/R$_2$/R$_3$ cyclic groups may be, but are not limited to: anthracene, bicyclo[4.4.0]decane, bicyclo[2.2.1]heptane, bicyclo[3.2.0]heptane, bicyclo[4.1.0]heptane, bicylo[2.2.1]hexane, bicyclo[4.3.0]nonane, bicyclo[2.2.2]octane, biphenyl, cyclopentadiene, cyclopentane, cyclobutane, cyclobutene, cycloheptane, cyclohexane, cyclooctane and cyclopropane, 1,2-diphenylethane, fluorene, indene, phenyl, terphenyl, napthalene, phenanthrene, terphenyl, toluene and xylene. Due primarily to availability and ease of synthesis, more preferred R/R$_1$/R$_2$/R$_3$ cyclic groups include less complex ring systems, such as, for example, cyclopentane and cyclohexane, cyclopentadiene, phenyl, indene, toluene and xylene.

R/R$_1$/R$_2$/R$_3$ heterocyclic groups may include azetidine, benzofuran, enzothiophene, carbazole, furan, glutarimide, indole, isoquinolone, lactam, lactone, oxazole, oxetane, oxirane, pyrrolidine, pyran, piperidine, pyridine, pyrrole, quinolone, tetrahydrofuran, tetrahydropyran, tetrahydrothiophene, thiophene, derivatives thereof and the like. Preferred R/R$_1$/R$_2$/R$_3$ heterocyclic groups are furan, indole, thymine and xanthine, although other heterocyclic groups are within the scope of the inventive compounds.

A non-cyclic core moiety may include, but is not limited to, for example, acetamide, amide, amine, amino acid (one or two), carboxide, ester, terminal halogen or hydrogen atom, hydroxide, glutaric acid, glycine derivative, ketone, phosphate, phosphonate, sulfate, sulfonate, sulfone, sulfoxide, simple ionic functional group, thiol or thiolester. Exemplary core moiety amino acids may include one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be an amide, carboxyl ester, carboxide, hydrogen, hydroxide or a dipeptide comprising two amino acids selected from the foregoing exemplary list. A non-cyclic, halogen, core moiety may be, for example, bromine, chlorine, fluorine and iodine.

A cyclic core may be at least one five- to seven-member non-heterocyclic ring or a heterocycle. The at least one five- to seven-membered non-heterocyclic ring may preferably have preferably have from one to three, five- to six- membered ring structures in a predominantly planar configuration. For example, the core moiety may be selected from the group consisting of substituted or unsubstituted benzene; biphenyl; cyclohexane; cyclohexanedione; cyclopentanedione; napthlalene; phenol; salicylic acid and derivatives thereof; stilbene or tricyclododecane.

Although other heterocyclic cores are within the scope of the invention, the following cores are representative heterocyclic cores: substituted or unsubstituted barbituric acid; benzamide; lactam; glutarimide; homophthalimide; hydrophthalimide; imidazole; imidazole amide; indomethacin; isocarbostyril; lumazine; N-allylheterocyclic; N-heterocyclic; pteridine; pthalimide; piperidine; pyridine; pyrimidine; pyrrole amide; quaternized N-heterocyclic; quinolizinedione; quinazolinone; quinolone; recorsinol; succinimide; theobromine; thymine; triazine; uric acid; uracil; vitamins A, E or K; or xanthine.

Non-limiting, representative substituents for the non-heterocyclic ring and heterocyclic cores include, but are not limited to, amide, primary, secondary and tertiary amine, C$_{(2-8)}$ alkenyl, C$_{(1-8)}$ alkyl (including, e.g., branched and unbranched alkyl or alkenyl groups), C$_{(1-8)}$ alkoxy, azide, carbonate, carbonyl, carboxylic acid, cyanide, C$_{(1-8)}$ haloalkyl (including, e.g., mono-, di- and tri-haloalkyl substituents, such as trihalomethyl), isocyanate, isothiocyanate, phosphate, phosphonate, primary, secondary or tertiary alcohol (including, e.g., any one of various diols, methanol, butanol, 1-cyclopentanol, ethanol, 2-ethyl-3-methyl- I -propanol, pentanol, propanol, and methylcyclohexanol), sulfonate, sulfone, sulfoxide, thioamide, thiocarbonate, thioester, thiolester, thiol, thiourea and urea.

Preferred cyclic and heterocyclic cores include substituted or unsubstituted glutarimide, methylthymine, methyluracil, thymine, theobromine, uracil and xanthine, most preferably halogen-substituted xanthine. Exemplary preferred cores include: 1,3-cyclohexanedione, 1,3-cyclopentanedione; 1,3-dihydroxynaphthalene; 1-methyllumazine; methylbarbituric acid; 3,3-dimethylglutarimide; orotic acid; tetra or hexahydrophthalimide; orthophenol; prostacyclin; 2-hydroxypyridine; methyldihydroxypyrazolopyrimidine, specifically, 1,3-dimethyldihydroxypyrazolo[4,3-d]pyrimidine; methylpyrrolopyrimidine; 1-methylpyrrolo[2,3-d]pyrimidine; 1,3-dihydroxynapthalene; 1-pyrrole amides; 2-pyrrole amides; 3-pyrrole amides; 1,2,3,4-tetrahydroisoquinolone; 1-methyl-2,4(1H,3H)-quinolizinedione (1-methylbenzoyleneurea); quinazolin-4(3H)-one; sulindac; dihydrothymine; alkyl-substituted (C1-6) thymine; 2,4-dioxohexahydro-1.3.5tetraziine; methylthymine; alkyl-substituted (C1-6) uracil; uracil fused to naphthalene; 6-aminouracil; 1-methyl-5,6-dihydrouracil; 1-methyluracil; 5- and/or 6-position substituted uracils (such as, for example, 5-bromouracil); B-ionone as vitamin A; 2,6,6-methyl-1-cyclohexene-1-acetaldehyde as vitamin A; tetralone to vitamin K; 1,7-dimethylxanthine, 3,7-dimethylxanthine; 3-methylxanthine; 3-methyl-7-methylpivaloylxanthine; 8-substituted xanthines (having substituents such as N or S); and 7-methylhypoxanthine.

Preferably, R is bonded to a nitrogen of the core moiety, most preferably the core moiety is xanthine and R of formula I is bonded to an N$_1$ xanthine nitrogen and N$_3$ and N$_7$ xanthine nitrogens are independently substituted by a member selected from the group consisting of hydrogen, methyl, fluoro, chloro and amino. Representative, preferred inventive compounds are compounds of formula II:

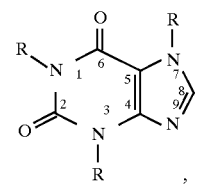

wherein R is defined above. A single R of formula I above may be bonded to the N$_1$ xanthine nitrogen or each of two R of formula I may be bonded to N$_1$ and N$_7$ xanthine nitrogens, respectively, in a covalent bond, or by an ether, ester, or peptide linkage. Preferably, one R$_1$ of —C(R$_1$)$_2$ is =N—OR$_2$, R$_2$ is hydrogen or methyl, the second R$_1$ is a C$_{(1-10)}$ alkyl (preferably methyl) or C$_{(1-10)}$ alkoxy. Especially preferred are compounds wherein (CH$_2$)$_n$ has one cis double bond between the third -and fourth carbon atoms, counting from a ring nitrogen toward the end of the R of formula I. Remaining preferred R substituents of formula II may be selected from the group consisting of hydrogen, methyl, fluorine, chlorine and amino.

The present invention further provides pharmaceutical compositions suitable for normal routes of therapeutic administration, providing effective compound dosages. The inventive pharmaceutical compositions comprise inventive compound and a pharmaceutically acceptable excipient, formulated for, e.g., parenteral, oral, topical and other known methods of pharmaceutical administration.

More specifically, the invention provides for a pharmaceutical composition comprising one or a plurality of inventive compounds and a pharmaceutically acceptable carrier or excipient. The individuals to be treated with an inventive compound or inventive pharmaceutical composition may either be contacted with the compound of the invention in vitro culture, in an extracorporeal treatment, or by administering (oral, parenteral or topical) the compound of the invention or pharmaceutical composition to a subject whose cells are to be treated.

Illustrative compounds of the invention include both syn and anti enantiomers and/or diastereomers, hydrates, salts, solvates and mixtures thereof, are representative only and are not intended as limiting the disclosure herein in any way:

1521  1-(5-Oximinohexyl)-3, 7-dimethylxanthine

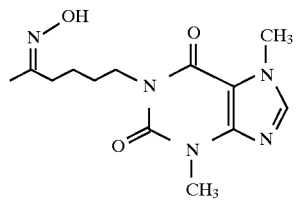

1522  1-(5-Methoximinohexyl)-3, 7-dimethylxathine

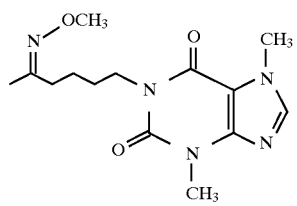

2514  1-(10-Oximinoundecyl)-3, 7-dimethylxanthine

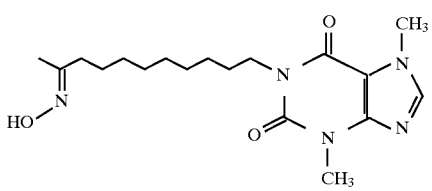

2525  1-(11-Oximinoundecyl)-3, 7-dimethylxanthine

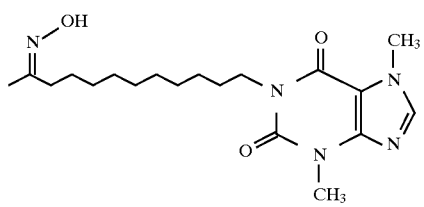

2597  1-(11-Octyloxy, -10-oximinoundecyl)-3, 7-dimethylxanthine

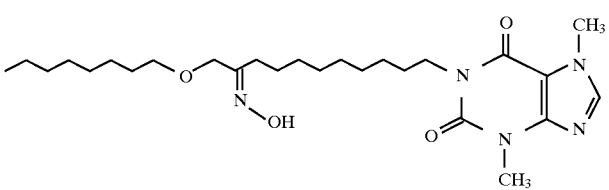

3513  1-(13-Oximinotetradecyl)-3, 7-dimethylxathine

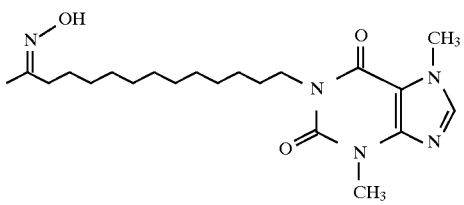

3522  1-(16-Oximinoheptadecyl)-3, 7-dimethylxanthine

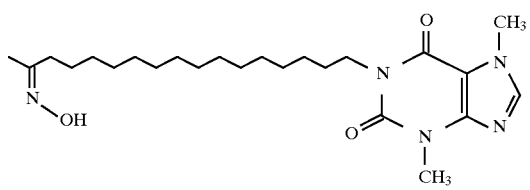

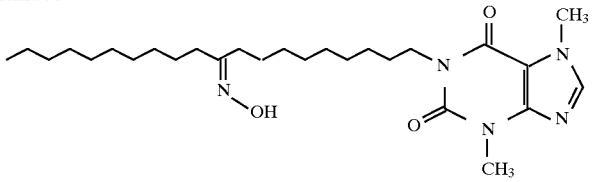

Uses of the Invention Compounds and Pharmaceutical Formulations

The compounds of the invention provide a mechanism to maintain homeostasis in cells contacted by primary stimuli through mitigating the effects of these primary stimuli on the secondary signaling pathways invoked within seconds of the primary stimulus. For example, administration of the inventive compounds in vivo or ex vivo provide a method to modify cellular behavior which method comprises contacting cells whose behavior is to be modified with an effective amount of an inventive compound or a pharmaceutical composition thereof wherein said method is: (1) a method to inhibit proliferation of tumor cells and said amount is sufficient to inhibit said proliferation; or a method to promote differentiation of hematopoietic stem cells into red blood cells, platelets, lymphocytes, and granulocytes, and said amount is sufficient to promote said proliferation; or (3) a method to suppress activation of T-cells by antigen or IL-2 stimulation, and said amount is sufficient to promote said activation; or (4) a method to suppress activation of monocyte/macrophage cells by endotoxin, TNF, IL-1 or GM-CSF stimulation and said amount is sufficient to suppress said activation; or (5) a method to enhance the resistance of mesenchymal cells to the cytotoxic effect of tumor necrosis; factor and said amount is sufficient to enhance said resistance; or (6) a method to suppress antibody production of B-cells in response to an antigen, IL-4 or CD40 ligand and said amount is sufficient to suppress said antibody production; or (7) a method to inhibit the proliferation of smooth muscle cells in response to growth factors capable of stimulating said proliferation and said amount is sufficient to inhibit said proliferation; or (8) a method to lower systemic vascular resistance conferred by endothelial cells and said amount is sufficient to reduce the release of hypertension-inducing substances; or (9) a method to lower systemic vascular resistance induced by endothelial cells and said amount is sufficient to enhance the release of anti-hypertensive substances; or (10) a method to lower expression of adhesion molecules induced by enhancers thereof, and said amount is sufficient to lower said expression; or (11) a method to suppress the activation of T-cells by HIV and said amount is sufficient to suppress said activation thus inhibiting viral replication; or (12) a method to inhibit the proliferation of kidney mesangial cells in response to stimulation by IL-1 and/or mip-1α and/or PDGF and/or FGF and said amount is sufficient to inhibit said proliferation; or (13) a method to enhance the resistance of kidney glomerular or tubular cells to cyclosporin A or amphotericin B and said amount is sufficient to enhance said resistance; or (14) a method to prevent the suppression of growth stimulatory factor production in TNF-treated bone marrow stromal cells and said amount is sufficient to prevent said suppression; or (15) a method to prevent the release of mip4a by IL-1 , TNF, or endotoxin stimulated monocytes and macrophages; or (16) a method to prevent the release of platelet activating factor by IL-1, TNF, or endotoxin treated megakaryocytes, fibroblastic cells, and macrophages; or (17) a method to prevent the down-regulation of receptors for cytokines in TNF-treated hematopoietic progenitor cells and said amount is sufficient to prevent said down-regulation; or (18) a method to suppress the production of metalloproteases in IL-1-stimulated or TNF-stimulated glomerular epithelial cells or synovial cells and said amount is sufficient to enhance said production; or (19) a method to enhance the resistance of gastrointestinal or pulmonary epithelial cells to cytotoxic drugs or radiation and said amount is sufficient to enhance said resistance; or (20) a method to enhance the antitumor effect of a non-alkylating antitumor agent and said amount is sufficient to enhance said effect, or (21) a method to inhibit the production of osteoclast activating factor in response to IL-1, and said amount is sufficient to inhibit said production, or (22) a method to inhibit degranulation in response to IgE, and said amount is sufficient to inhibit said degranulation, or (23) a method to enhance the release of adrenergic neural transmitters, dopamine, norepinephrine, or epinephrine, or the neurotransmitter, acetylcholine, and said amount is sufficient to enhance said release, or (24) a method to modulate the post-synaptic "slow current" effects of the adrenergic neurotransmitter dopamine, epinephrine, or norepinephrine, or the neurotransmitter acetylcholine, and said amount is sufficient to modulate such slow currents.

For example, the compounds of the invention are used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy with or without total body irradiation that exceed the lethal dose for normal bone marrow recovery. This provides the rationale for using either stored patient marrow or donor marrow to rescue the patient. In general, chemotherapy and radiation are delivered to the patient for 7–10 consecutive days before the new or stored bone marrow is infused. The day on which the marrow is given to the patient is referred to as day 0 of the transplant. Previous days on which the patient received chemo/radiation are designated by negative numbers. Subsequent days are referred to by positive numerals.

The median time in which negative responses in BMT recipients occurs is within the first 100 days after transplant. Therefore, statistically, if patients survive through day 100, their chances for continued survival are significantly enhanced. Compounds of Formula 1 are able to increase the percentage of patients who survive. The percentage of fatalities within the first 100 days that is considered acceptable is 15–20% for "good risk" patients and 30–40% for "high risk". These fatalities are due to the direct effects of high doses of chemo/radiation. In addition, GVHD contributes to the death rate in allogeneic marrow recipients.

Other indications for which it is useful to administer the compounds of the invention include the presence of a tumor burden, a hormone-related disorder, a neurological disorder, an autoimmune disease, inflammation, restenosis, hypertension, unwanted immune response, viral infection, nephritis, mucositis, and various allergic responses. Prevention of allergic responses include prevention of acute allergic response and thus moderation or prevention of rhinorrhea, sinus drainage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEVI, changes in vital capacity, and extensive mucus production.

Other suitable subjects for the administration of compounds of the invention, include patients being administered cytoreductive agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering; from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T and B cells, and patients who have neurological disorders.

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiring such treatment as an effective oral, parenteral, or intravenous sublethal dose of about 50 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Pharmaceutical Formulations

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water with a flavor or coloring agent.

The amount of inventive compound required for therapeutic effect on topical administration will, of course, vary with the compound chosen, the nature and severity of the disease and the discretion of the treatment provider. Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier optionally containing a parenterally acceptable oil, for example polyethylene glycol, polyvinylpyrrolidone, lecithin, arachis oil, or sesame oil. The daily dosage for treatment of sepsis or another severe inflammatory condition via parenteral administration is suitable from about 0.001 mg/kg to about 40 mg/kg, preferably from about 0.01 mg/kg to about 20 mg/kg of an inventive compound or a pharmaceutically acceptable salt thereof calculated as the free base.

The inventive compounds may be administered orally. The daily dosage regimen for oral administration is suitably from about 0.1 mg/kg to about 1000 mg/kg per day. For administration the dosage is suitably from about 0.001 mg/kg to about 40 mg/kg of the inventive compound or a pharmaceutically acceptable salt thereof calculated as the free base. The active ingredient may be administered from 1 to 6 times a day, sufficient to exhibit activity.

The inventive compounds may be administered by inhalation (e.g., intranasal or oral). Appropriate dosage forms include an aerosol or a metered dose inhaler, as prepared by conventional techniques. The daily dosage is suitably from about 0.001 mg/kg to about 40 mg/kg of the inventive compound or a pharmaceutically acceptable salt thereof calculated as the free base. Typical compounds for inhalation are in the form of a solution, suspension or emulsion that may be administered as a dry powder or in the form of an aerosol using a conventional propellant.

The following examples, which should not be regarded as limiting in any way, illustrate the invention.

EXAMPLE 1

This example illustrates a method for synthesis of inventive compound no. 1521 (see above for chemical name and formula. A 10% aqueous solution of sodium hydroxide (10 ml) was added to a mixture of pentoxifylline (1.39 g, 5 mmol) and hydroxylamine hydrochloride (521 mg, 7.5 mmol) and stirred for 24 hours. The reaction mixture was treated with water (50 ml) and then extracted with dichloromethane (3×50 ml). The organic portions were combined, dried under sodium sulfate and the solvents evaporated under vacuum to obtain 1.2 g of a white powder, a 1:4 syn/anti mixture of compound no. 1521 (82% yield).

EXAMPLE 2

This example illustrates a method for synthesis of inventive compound no. 1522 (see above for chemical name and formula. Pentoxifylline (55 mg, 2 mmol), methoxyamine hydrochloride (186 mg, 2.2 mmol) and pyridine (0.17 ml) were added to a glass reaction vessel containing methanol (10 ml). The mixture was stirred at room temperature for one hour. Subsequently, the solvent was evaporated. Water (15 ml) was added to the residue and this mixture was extracted with dichloromethane (2×30 ml). The organic portions were dried over magnesium sulfate, and the solvent removed by rotary evaporation, leaving 601 mg of a white solid, a syn/anti mixture of compound no. 1522 isomers (97% yield).

EXAMPLE 3

This example illustrates a method for synthesis of an intermediate compound, 1-(10,11-oxidoundecanyl)-3,7-dimethylxanthine, used in subsequent synthesis of inventive compounds nos. 2514, 2597 and 3526.

Sodium hydride(95%, 1.26 g, 50 mmol) was added to a solution of theobromine (7.2g, 40 mmol) in dimethylsulfoxide (300 mL). After 20 minutes of stirring, undecenylmesylate (7.95 g, 30 mmol) was added and the resulting mixture stirred for 12 hours at room temperature. The reaction was warmed to 70°–80° C. and stirred for 4 hours. The reaction mixture was then poured into a separatory funnel containing 1 l of water and extracted with dichloromethane (5×200 ml). The organic extracts were combined, washed with water (100 me) and brine (100 ml), dried over anhydrous magnesium sulfate and concentrated under reduced pressure. The crude product obtained was further purified by flash chromatography over silica gel using a 20% hexane/dichloromethane eluant, producing 4.6 g of 1-(10-undecenyl)-3,7-dimethylxanthine01 (46.3% yield).

A solution of 1-(10-undecenyl)-3,7-dimethylxanthine (4.3 g, 13 mmol), 4-methylmorpholine-N-oxide (1.942 g, 16.6 mmol) and potassium osmate dihydrate (9.5 mg; 0.026 mmol) in acetone (45 ml) and water (10 ml) was stirred for 6 hours. A solution of 20% aqueous sodium sulphite (12 ml) was added and the resulting mixture stirred for 30 minutes. The reaction mixture was extracted with 25% ethanol/dichloromethane (4×100 ml). The combined organic extracts were dried over anhydrous magnesium sulfate concentrated under reduced pressure and purified by flash chromatography over silica gel using a methanol (5%)/dichloromethane eluant, producing 3.6 g of 1-(10,11-dihydroxyundecanyl)-3,7-dimethylxanthine (76% yield).

1-(10,11-Dihydroxyundecanyl)-3,7-dimethylxanthine (3.6 g, 10 mmol) was stirred with hydrogen bromide (6.2 ml, 8.4 g of a 30% solution in acetic acid, 31.1 mmol) for 90 minutes. The mixture was then added to a flask containing 100 ml aqueous sodium bicarbonate solution and 75 ml dichloromethane. After 10 minutes of vigorous stirring, the layers were separated and the aqueous portion washed with dichloromethane (3×75 ml). The organic portions were combined, dried over magnesium sulfate, and evaporated to give 1-(10-acetoxy-11-bromoundecanyl)-3,7-dimethylxanthine (3.6 g). Without further purification, the bromoacetate was taken up in methanol (25 ml) and treated with a solution of sodium methoxide (prepared from 0.28 g, 12.2 mmol sodium, and 25 ml methanol). After 30 minutes most of the solvent was removed under reduced pressure and the residue was extracted with dichloromethane (3×75 ml). The organic portions were combined, dried over magnesium sulfate and concentrated under reduced pressure to give an off-white solid. Subsequent purification by column chromatography over silica gel using a dichloromethane/(3%) methanol eluant produced 2.0 g of 1-(10,11-oxidoundecanyl)-3,7-dimethylxanthine (57.5% yield).

EXAMPLE 4

This example illustrates a synthetic protocol for inventive compound no. 2514 (see above for chemical name and formula). 348 mg (1 mmol) of 1-(10,11-oxidoundecanyl)-3,7-dimethylxanthine, prepared in example 3 above, was added to a suspension of sodium borohydride (115.6 mg; 3 mmol) in 10 ml of ethanol. The reaction was warmed to 60° C. and stirred overnight. Most of the ethanol was removed under reduced pressure. A saturated $NH_4Cl$ solution (20 ml) was added and extracted with ethyl acetate (3×75 ml). The combined organic extracts were dried over anhydrous magnesium sulfate and concentrated under reduced pressure. The crude product obtained was further purified by flash chromatography over silica gel using a 3% methanol/dichloromethane eluant to obtain 237 mg of 1-(10-hydroxyundecanyl)-3,7-dimethylxanthine (68% yield).

Dimethylsulphoxide (102 mg; 1.3 mmol) was added dropwise to a solution of oxalyl chloride (91.7 mg; 0.72 mmol) in 5 ml of dry dichloromethane at −78° C. A solution of 1-(10-hydroxyundecanyl)-3,7-dimethylxanthine (0.23 g; 0.66 mmol) in 5 ml of dichloromethane was added and the resulting mixture stirred for 15 minutes. Triethylamine (0.332 mg; 3.29 mmol) was then added and the reaction warmed to room temperature. After stirring the reaction for an hour, the mixture was poured into 25 ml of water and extracted with 3×25 ml of dichloromethane. The combined organic extracts were successively washed with 1% hydrogen chloride (20 ml), saturated sodium bicarbonate solution (20 ml) and brine (20 ml), dried over anhydrous magnesium sulfate and concentrated under reduced pressure. The crude product obtained was further purified by flash chromatography over silica gel using a 20% hexane/ethyl acetate eluant, resulting in 150 mg of 1-(10-oxoundecanyl)-3,7-dimethylxanthine (65.8% yield).

A solution of sodium hydroxide (66 mg; 1.65 mmol) in 0.66 ml of water was added to a solution of 1-(10-oxoundecanyl)-3,7-dimethylxanthine, prepared above (115 mg, 0.33 mmol), and hydroxylaminehydrochloride 34.45 mg (0.49 mmol) in 3.3 ml of ethanol. The resulting reaction mixture was stirred overnight. The reaction mixture was diluted with water (10 ml) and extracted with dichloromethane (3×25 ml). The organic portions were combined, washed with saturated brine solution (25 ml), dried with magnesium sulfate and concentrated under reduced pressure. A crude product was purified by column chromatography over silica gel using a hexane (20%)/ethyl acetate eluant, producing 80 mg of inventive compound no. 2514 (66.6% yield).

EXAMPLE 5

This example illustrates a synthetic protocol for inventive compound no. 2525 (see above for chemical name and formula). To a suspension of magnesium (6.4 g, 265 mmol) and a crystal of iodine in tetrahydrofuran (40 ml) was added 10-undecenyl bromide (Syn. Comm. 1984, 14, 591–597: 12.25 g, 53.0 mmol) in tetrahydrofuran (30 ml) over 30 minutes and the reaction was stirred for a further 30 minutes after the addition was complete. The solution was added via a canula over 5 minutes to a suspension of paraformaldehyde (1.80 g, 60.0 mmol) in tetrahydrofuran (40 ml) and stirred at 25° C. for 16 hours. Saturated ammonium chloride (80 ml) was added and extracted with diethyl ether (2×100 ml). The combined organic extracts were dried (magnesium sulfate) and evaporated to give a residue which was distilled at 2 mm Hg, yielding a clear liquid alcohol, 11-dodecen-1-ol (6.53 g, 67 %, b.p. 105°–107° C.).

To a solution of 11-dodecen-1-ol (5.5 g, 29.9 mmol) in dichloromethane (70 ml) at 0° C. was added methanesulfonyl chloride (3.55 g, 2.40 ml, 31.0 mmol) followed by triethylamine (4.38 g, 46.0 mmol). After stirring for 10 minutes at 0° C., the reaction was allowed to warm to 25° C. and stirred for 2 hours. The reaction was poured into water (60 ml), separated and washed with dichloromethane (50 ml). The organic portions were combined, dried with magnesium sulfate, and evaporated, yielding 12-methanesulfonyl-1-dodecene as a yellow oil which was used without further purification. To a suspension of sodium theobromine (6.00 g, 30.0 mmol) in dimethylsulfoxide (60 mL) was added 12-methanesulfonyl-1-dodecene. The resulting reaction mixture was stirred for 16 hours at 60° C. The mixture was then poured into water (120 ml) and extracted with diethyl ether (2×100 ml). The organic portions were combined, dried with magnesium sulfate. The evaporated solvent left a cream-colored solid. Recrystallization from ethyl acetate/hexane (1:1) yielded 6.97 g of a white solid, 1-(11-dodecenyl)-3,7-dimethylxanthine as a white solid (67% yield).

A solution of 1-(11-dodecenyl)-3,7-dimethylxanthine, prepared above (4.70 g, 13.6 mmol), 4-methylmorpholine-N-oxide (4.79 g, 40.7 mmol) and potassium osmate dihydrate (52 mg, 0.14 mmol) in acetone/water 1:2 (75 ml) was stirred for 16 hours. Water (50 ml) and sodium sulfite (5 g) were subsequently added to the solution and the resulting reaction mixture stirred for 1 hour. The reaction mixture was extracted with dichloromethane (3×100 ml), dried using magnesium sulfate and the solvent evaporated, resulting in a pale, green solid. Recrystallization from hot ethyl acetate yielded 4.32 g of a white solid, 1-(11,12-dihydroxydodecyl)-3,7-dimethylxanthine (84% yield).

1-(11,12-Dihydroxydodecyl)-theobromine, prepared above (2.50 g, 6.58 mmol), was stirred with hydrogen bromide (6.39 ml of a 30% solution in acetic acid, 19.73 mmol) for 2 hours. The mixture was then added over 10 minutes to water (25 ml), ice (30 g) and sodium hydrideCO$_3$ (15 g). The resulting mixture was then stirred for 30 minutes. The mixture was extracted with dichloromethane (3×50 ml), and the organic phases combined and dried with magnesium sulfate. The solvent was evaporated to afford a residue (3.18 g, 99%) of 1-(11-acetoxy-12-bromododecyl)-3,7-dimethylxanthine. Without further purification, this crude product was taken up in methanol (10 ml) and treated with a solution of sodium methoxide (prepared from sodium, 0.160 g, 6.90 mmol, and 20 ml methanol). After 60 minutes, the reaction was added to water (30 ml) and extracted with dichloromethane (3×50 ml). The organic portions were combined, dried and evaporated t produce 2.20 g of a white solid, 1-(11,12-oxidododecyl)-3,7-dimethylxanthine (93% yield)

1-(11,12-Oxidododecyl)-3,7-dimethylxanthine (0.80 g, 2.21 mmol) was dissolved in ethanol (12 ml). Sodium borohydride (0.131 g, 3.54 mmol) was added and the resulting reaction stirred at 60° C. for 16 hours. Water (20 ml) and saturated brine (20 ml) were added and extracted with dichloromethane (80 ml, 50 ml). The combined extracts were dried with magnesium sulfate and evaporated to obtain 0.62 g of a white solid 1-(11-hydroxydodecyl)-3,7-dimethylxanthine (77% yield).

To a solution of oxalyl chloride (0.11 ml, 1.30 mmol) in dichloromethane (8 ml) at −78° C. was added dimethylsulfoxide (0.20 ml, 2.60 mmol) and over a 5 minute period 1-(1-hydroxydodecyl)-3,7-dimethylxanthine (0.40 g, 1.10 mmol) in dichloromethane (4 ml). The reaction was stirred at −78° C. for 30 minutes and after the addition of triethylamine (0.72 ml, 5.20 mmol), the reaction was allowed to warm to 25° C. over 30 minutes. Water (10 ml) was added, the organic phase separated and the aqueous phase washed with dichloromethane (10 ml). The organic portions were combined and dried with magnesium sulfate, and the solvent evaporated to give a slightly yellow solid. The crude yellow solid was recrystallized from hot hexane to obtain 0.32 g of a white solid, 1-(1-oxododecyl)-3,7-dimethylxanthine (80% yield).

To a solution of 0.16 g of 1-(11-oxododecyl)-3,7-dimethylxanthine, prepared above (0.44 mmol) in methanol (5 ml) was added pyridine (0.039 ml, 0.48 mmol) and hydroxylamine hydrochloride (0.034 g, 0.48 mmol). The solution was stirred for 1 hour. The solvent was evaporated and water (10 ml) added and product extracted with dichloromethane (2×10 ml). The organic extracts were combined and dried over magnesium sulfate. The evaporated solvent left 0.16 g of a white solid, a mixture of syn/anti isomers of inventive compound no. 2525 (96% yield).

EXAMPLE 6

This example illustrates a synthetic protocol for inventive compound no. 2597 (see above for chemical name and formula). Sodium hydride (312 mg, 13 mmol) was added to a solution of octanol (10 ml) in toluene (20 ml). After bubbling had ceased, 2.5 g of 1-(10,11-oxidoundecyl)-3,7-dimethylxanthine, prepared in Example 3 above (7.2 mmol) was added and the resulting mixture was stirred for 3 hours at 60°–70 ° C. After cooling, the mixture was added to a mixture of saturated aqueous solution of ammonium chloride (15 ml) and water (10 ml) and extracted with dichloromethane (3×50 ml). The combined organic layers were washed with saturated aqueous salt solution and dried over sodium sulfate. Evaporation of the solvents under vacuum gave a solid residue. The solid residue was purified using chromatography (neutral activity II alumina/dichloromethane) to obtain 411 mg of recovered epoxide and 1.34 g of 1-(11-octyloxy-10-hydroxyundecyl)-3,7-dimethylxanthine (49% yield).

Dimethylsulfoxide (0.18 ml, 2.5 mmol) was added slowly by syringe to a stirring solution of oxalyl chloride (0.11 ml, 1.3 mmol) in dichloromethane (5 ml) at −780° C. After 2 minutes, a solution of 1-(11-octyloxy-10-hydroxyundecyl)-3,7-dimethylxanthine, prepared above (0.5 g, 1.0 mmol) in dichloromethane (15 ml) was added dropwise over 5 minutes. Stirring was continued at −78° C. for 45 minutes. Triethylamine (0.72 ml, 5.2 mmol) was added and the cold bath subsequently removed. After 20 minutes, water (25 ml) was added and the mixture was extracted with dichloromethane (3×50 ml). The combined organic extracts were washed with saturated aqueous sodium bicarbonate (20 ml) and saturated aqueous salt solution (20 ml), and then dried over sodium sulfate. The solvents were evaporated under vacuum to give a thick oil which was purified by chromatography (silica/dichloromethane-5% methanol) to obtain 205 mg of 1-(11-octyloxy-10-oxoundecyl)-3,7-dimethylxanthine (43% yield).

A mixture of 1-(11 -octyloxy-10-oxoundecyl)-3,7-dimethylxanthine, prepared above (90 mg, 0.2 mmol), hydroxylamine hydrochloride (90 mg, 1.3 mmol) and pyridine (88 mg, 1.1 mmol) in ethanol (0.9 ml) was stirred and heated at 80° C. for 90 minutes. The solvent was removed under vacuum and the residue was washed with 0.9 ml water. The residue was subsequently purified by chromatography on silica using an ethyl acetate eluant to obtain 52 mg of compound no. 2597.

EXAMPLE 7

This example illustrates a synthesis for inventive compound no. 351 3. To a suspension of magnesium (1.86 g, 77.2 mmol) and a crystal of iodine in THF (20 ml) was added 10-undecenyl bromide (6.00 g, 25.8 mmol) in THF (14 m) over 40 minutes and the reaction stirred for a further 30 minutes after completion of the addition. The solution was added via a canula over 50 minutes to a suspension of copper iodide (0.50 g, 2.58 mmol) and 1-bromo-3-chloropropane (3.84 ml, 38.7 mmol) in THF (20 ml) and stirred at 25° C. for 16 hours. Sulfuric acid (1.0 M, 50 ml) was added, extracted with diethyl ether (2×60 ml) and the organic solvent was dried over magnesium sulfate and subsequently evaporated The residue was distilled at 0.25 mmHg, producing 3.06 g of 13-tetradecenyl chloride as a colorless liquid (51% yield, b.p. 98°–100° C.).

To a suspension of sodium theobromine (1.82 g, 8.68 mmol) in dimethylsulfoxide (20 ml) was added 13-tridecenyl chloride. The resulting reaction mixture was stirred for 48 hours at 50° C. The mixture was then poured into water (60 ml) and extracted with ethyl acetate (3×50 ml). The organic portions were combined, dried over magnesium sulfate, and the solvent evaporated, leaving a cream-colored solid. Recrystallisation of the solid from hot hexane yielded 2.38 g of 1-(13-tetradecenyl)-3,7-dimethylxanthine as a white solid (73% yield).

A solution of 1-(13-tetradecenyl)-3,7-dimethylxanthine (2.00 g, 5.35 mmol), 4-methylmorpholine-N-oxide (2.72 ml, 60% wt. in water, 15.8 mmol) and potassium osmate dihydrate (21 mg, 0.05 mmol) in acetone/water, in a ratio of 3:1 (80 mL), was stirred for 16 hours. Water (100 ml) and sodium sulfite (1 g) were added and stirred for 1 hour. The reaction mixture was extracted with dichloromethane (3×100 ml) and the organic phase dried over magnesium sulfate. The solvent was evaporated to obtain 2.1 g of 1-(13,14-dihydroxytetradecyl)-3,7-dimethylxanthine as a white solid (96% yield).

To a solution of oxalyl chloride (0.031 mL, 0.35 mmol) in dichlorornethane (2 ml) at −78° C. was added dimethylsulfoxide (0.055 mL, 0.70 mmol) and over a 5 minute period 1-(13,14-hydroxytetradecyl)-3,7-dimethylxanthine (0.11 g, 0.29 mmol) in dichloromethane (2 ml). The resulting reaction was stirred at −78° C. for 30 minutes, and after the addition of triethylamine (0.19 ml, 1.40 mmol), allowed to warm to 25° C. over 30 minutes. Hydrochloric acid (1.0M, 10 ml) and dichloromethane (5 ml) were added, the organic phase was separated and the aqueous phase was washed with dichloromethane (10 ml). The organic portions were combined and dried over magnesium sulfate and the solvent was evaporated to obtain a slightly yellow solid. Upon purification by chromatography (silica, ethyl acetate), 0.056 g of 1-(13-oxotetradecyl)-3,7dimethylxanthine was obtained as a white solid (50% yield).

To a solution of 1-(13-oxotetradecyl)-3,7-dimethylxanthine, prepared above (0.040 g, 0.10 mmol), in methanol/dichloromethane (2:5, 7 ml) was added pyridine (0.010 ml, 0.12 mmol) and hydroxylamine hydrochloride (0.009 g, 0.12 mmol). The resulting mixture was stirred for 1 hour. Water (10 ml) was added and the organic component of the reaction mixture extracted with dichloromethane (2×10 ml). The organic extracts were combined, dried over magnesium sulfate and the remaining solvent evaporated to obtain 0.032 g of compound no. 3513 as a white solid mixture of syn/anti enantiomenrs (79% yield).

EXAMPLE 8

This example illustrates a synthetic protocol for inventive compound no. 3522 (see above for chemical name and formula). To a suspension of magnesium (3.10 g, 129 mmol) and a crystal of iodine in THF (10 ml) was added 10-undecenyl bromide (see: Syn. Comm. 1984, 14, 591–597) (6.00 g, 25.8 mmol) in THF (20 ml) over 40 minutes. The resuling reaction mixture was stirred for a further 30 minutes after the addition was complete. The solution was added via a canula over 50 minutes to a suspension of copper iodide (0.50 g, 2.58 mmol) and 1-bromo-6-chloro hexane (6.00 ml, 40.0 mmol) in THF (20 ml) and stirred at 25° C. for 16 hours. Sulfuric acid (1.0M, 50 ml) was added, extracted with diethyl ether (2×60 ml) and the organic solvent was dried over magnesium sulfate and evaporated. The residue was distilled at 0.75 mmHg, resulting in 1.78 g of 16-heptadecenyl chloride as a colourless liquid (25% yield, b.p. 130°–135° C.).

To a suspension of sodium theobromine (2.02 g, 10.0 mmol) in dimethylsulfoxide/tetrahydrofuran (2:1, 30 ml) was added 16-heptadecenyl chloride and the reaction stirred for 16 hours at 60° C. The mixture was then poured into water (75 ml) and extracted with ethyl acetate (3×75 ml). The organic portions were combined, dried over magnesium sulfate and the solvent evaporated, leaving a cream-colored solid residue. Recrystallization of the residue from hot hexane resulted in 2.31 g of 1-(16-Heptadecenyl)-3,7-dimethylxanthine as a white solid (85% yield).

A solution of 1.5 g of 1-(16-Heptadecenyl)-3,7-dimethylxanthine (3.60 mmol), 4-methylmorpholine-N-oxide (1.83 ml, 60% wt in water, 10.6 mmol) and potassium osmate dihydrate (16 mg, 0.04 mmol) in acetone/water/tetrahydrofuran (10:7:5, 110 ml) was stirred for 60 hours. Water (100 ml) and sodium sulfite (1 g) were added and the resulting reaction mixture stirred for 1 hour. The reaction mixture was extracted with dichloromethane (2×100 ml) and the organic phase dried over magnesium sulfate. The evaporated solvent left a cream-colored solid. Recrystallization of the crude solid from hot ethyl acetate produced 1.31 g of 1-(16,17-dihydroxyheptadecyl)-3,7-dimethylxanthine as a white solid (81% yield).

1.10 g of 1-(16,17-dihydroxyheptadecyl)-3,7-dimethylxanthine (2.44 mmol) was stirred with HBr (3.50 ml of a 30% solution in acetic acid, 17.1 mmol) for 4 hours. The mixture was then added over 10 minutes to water (50 ml) and NaHCO3 (10 g), and the resulting mixture stirred for 30 minutes. The organic component was extracted with dichloromethane (3×30 ml), and the combined organic phase was dried over magnesium sulfate. The evaporated solvent left a residue of 1-(16-acetoxy-17-bromoheptadecyl)-3,7-dimethylxanthine. Without further purification, this crude product was taken up in methanol (5 ml) and treated with a solution of sodium methoxide (prepared from sodium, 0.074 g, 3.20 mmol, and 5 ml methanol). After 40 minutes, the reaction was added to water (15 ml) and extracted with dichloromethane (3×30 ml). The organic portions were combined, dried and the solvent evaporated, leaving 1.0 g of 1-(16,17-oxidoheptadecyl)-3,7-dimethylxanthine (95% yield), as a white solid.

0.25 g of 1-(16,17-oxidoheptadecyl)-3,7-dimethylxanthine (0.58 mmol) was dissolved in ethanol (5 ml). Sodium borohydride (0.34 g, 0.93 mmol) was added to the ethanol solution and the reaction stirred at 60° C. for 16 hours. Hydrochloric acid (1.0M, 10 ml) was added and extracted with dichloromethane (2×30 ml). The combined extracts were dried over magnesium sulfate. Evaporated solvent left 0.225 g of 1-(16-hydroxyheptadecyl)-3,7-dimethylxanthine as a white solid (90% yield).

To a solution of oxalyl chloride (0.036 ml, 0.41 mmol) in dichloromethane (3 ml) at −78° C. was added dimethylsulfoxide (0.063 ml, 0.82 mmol), and over 5 minutes, 1-(16-hydroxyheptadecyl)-3,7-dimethylxanthine (0.15 g, 0.35 mmol) in dichlorornethane (2 ml). The resulting reaction mixture was stirred at −78° C. for 30 minutes, and after the addition of triethylamine (0.23 ml, 1.64 mmol), was allowed to warm to 25° C. olier 30 minutes. Hydrochloric acid (1.0M, 10 ml) and dichloromethane (5 ml) were added to the warmed reaction mixture. The organic phase was separated and the aqueous phase was washed with dichlorornethane (10 ml). The organic portions were combined, dried over magnesium sulfate and evaporated to obtain a slightly yellow solid. The yellow solid, purified by chromatography (silica, ethyl acetate/hexane) resulted in 0.070 g of 1-(16-oxoheptadecyl)-3,7-dimethylxanthine as a white solid (47% yield).

To a solution of 1-(16-oxoheptadecyl)-3,7-dimethylxanthine, prepared above (0.026 g, 0.060 mmol), in methanol/dichloromethane (1:1, 6 ml) was added pyridine (0.006 ml , 0.07 mmol) and hydroxylamine hydrochloride (0.005 g, 0.07 mmol). The resulting solution was stirred for 1 hour. Water (10 ml) was added and extracted with dichloromethane (2×10 ml). The organic extracts were combined and dried over magnesium sulfate. The solvent was evaporated, leaving 0.023 g of a white solid, compound no. 3522 as a mixture of synlanti enantiomers (81% yield).

EXAMPLE 9

This example illustrates a synthetic protocol for inventive compound no. 3526 (see above for chemical name and formula). To a suspension of copper iodide (0.095 g, 0.50 mmol) in tetrahydrofuran (16 ml) at −40° C. was added nonylmagnesium bromide (8 ml, 0.31M solution in tetrahydrofuran, 2.50 mmol). The resulting mixture was stirred for 40 minutes at −40° C. A solution of 0.70 g of 1-(10,11-oxidoundecanyl)-3,7-dimethylxanthine (2.00 mmol) in dry tetrahydrofuran (10 ml) was added to the mixture and the mixture stirred at −40° C. for 90 minutes. Hydrochloric acid (1.0M, 10 ml) was added, extracted with dichloromethane (2×30 ml) and the solvent dried over magnesium sulfate and evaporated. The residue was purified by column chromatography (ethyl acetate) to obtain 0.25 g of 1-(10-hydroxyeicosyl)-3,7-dimethylxanthine as a white solid (27% yield).

To a solution of oxalyl chloride (0.036 ml, 0.41 mmol) in dichloromethane (3 ml) −78° C. was added dimethylsulfoxide (0.063 ml, 0.82 mmol), and over 5 minutes, 1-(10-hydroxyeicosyl)-3,7-dimethylxanthine (0.135 g, 0.28 mmol) in dichloromethane (2 ml). The reaction was stirred at −78° C. for 30 minutes and after the addition of triethylamine (0.23 ml, 1.64 mmol) allowed to warm to 25° C. over 30 minutes. Hydrochloric acid (1.0M, 10 ml) and dichloromethane (5 ml) were added, the organic phase separated and the aqueous phase washed with dichloromethane (10 ml). The organic portions were combine and dried over magnesium sulfate. Evaporating the solvent left a slightly yellow solid, which upon purification by chromatography (silica, ethyl acetate) produced 0.110 g of 1-(10-oxoeicosyl)-3,7-dimethylxanthine as a white solid (85% yield).

To a solution of 1-(10-oxoeicosyl)-3,7-dimethylxanthine, prepared above (0.039 g, 0.082 mmol), in methanol/dichloromethane (1:1, 6 ml) was added pyridine (0.008 ml, 0.10 mmol) and hydroxylamine hydrochloride (0.007 g, 0.10 mmol). The resulting reaction mixture was stirred for 1 hour. Water (10 ml) was added and extracted with dichloromethane (2×10 ml). The organic extracts were combined and dried over magnesium sulfate. Evaporating the solvent left 0.034 g of white solid, a mixture of syn/anti isomers of inventive compound 3526 (86% yield).

EXAMPLE 10

Example 10 illustrates a mixed lymphocyte reaction of inventive compounds nos. 1521 and 1522 (see above for chemical name and structure). The mixed lymphocyte reaction shows a proliferative response of PBMC (peripheral blood mononuclear cells) to allogeneic stimulation determined in a two-way mixed lymphocyte reaction. Assay results are reported in FIG. 1. Both compounds nos. 1521 and 1522 showed activity in this immune modulating activity assay procedure.

EXAMPLE 11

Figure 2:
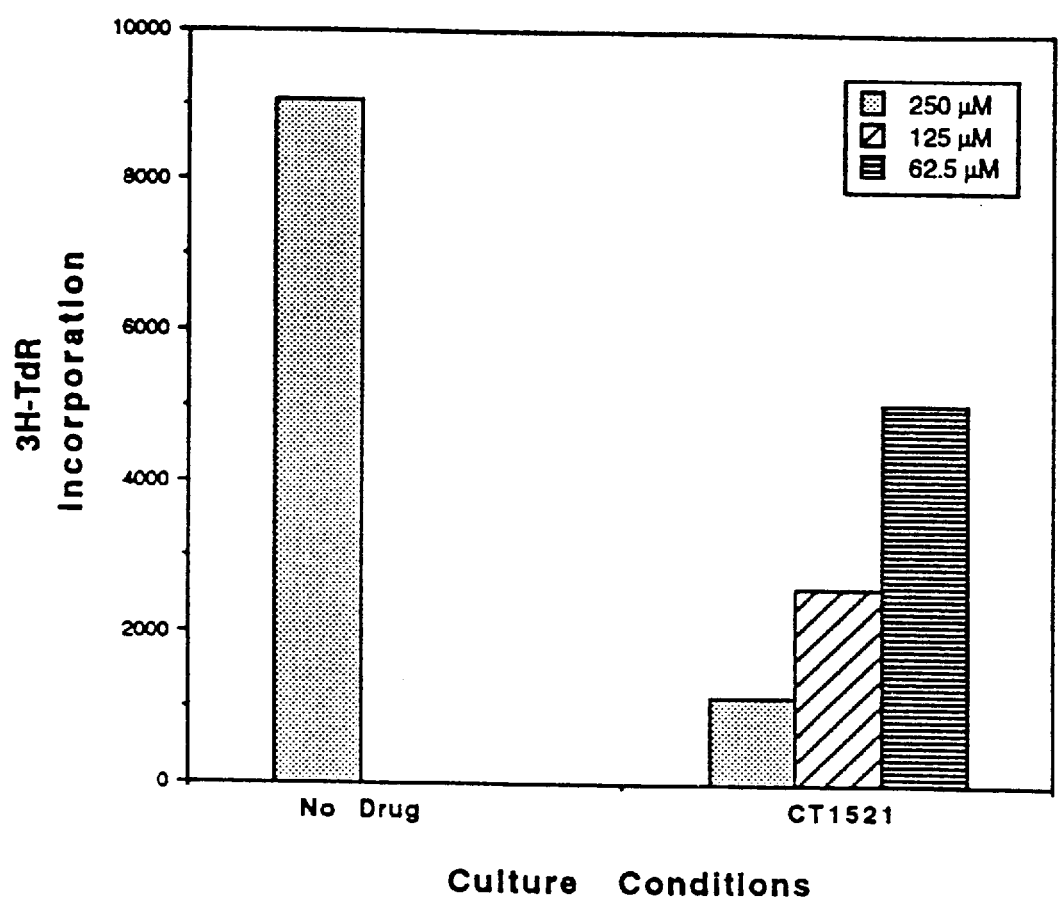
FIG. 2 shows the effects of inventive compound no. 1521 on inhibition of murine thymocyte proliferation stimulated by Concanavalin A (ConA) and interleukin-1 alpha (IL-1α). Background counts in this investigation were less than 200 cpm.

This example shows the effects of inventive compound no. 1521 on inhibition of murine thymocyte proliferation stimulated by Concanavalin A (ConA) and interleukin-I alpha (IL-1α). Thymuses were obtained from normal, female Balb/C mice. The thymuses were dissociated and plated into 96-well plates at a density of 2×10$^5$ cells/well. ConA and IL-1α were added to the wells (ConA (0.25 μg/ml) and IL-1α (12.5 ng/ml)). The cells were incubated for 4 days at 37° C. On day 4, the cells were pulsed with tritiated thymidine and allowed to incubate for an additional 4 hours. The cells were harvested and incorporated tritiated thymidine was determined in a liquid scintillation counter. Drug was added at the doses indicated two hours prior to activation with ConA an IL-1α. Compound no. 1521 inhibited thymocyte proliferation in a dose-response manner a is shown in FIG. 2. Background counts were less than 200 cpm.

33

EXAMPLE 12

Figure 3:
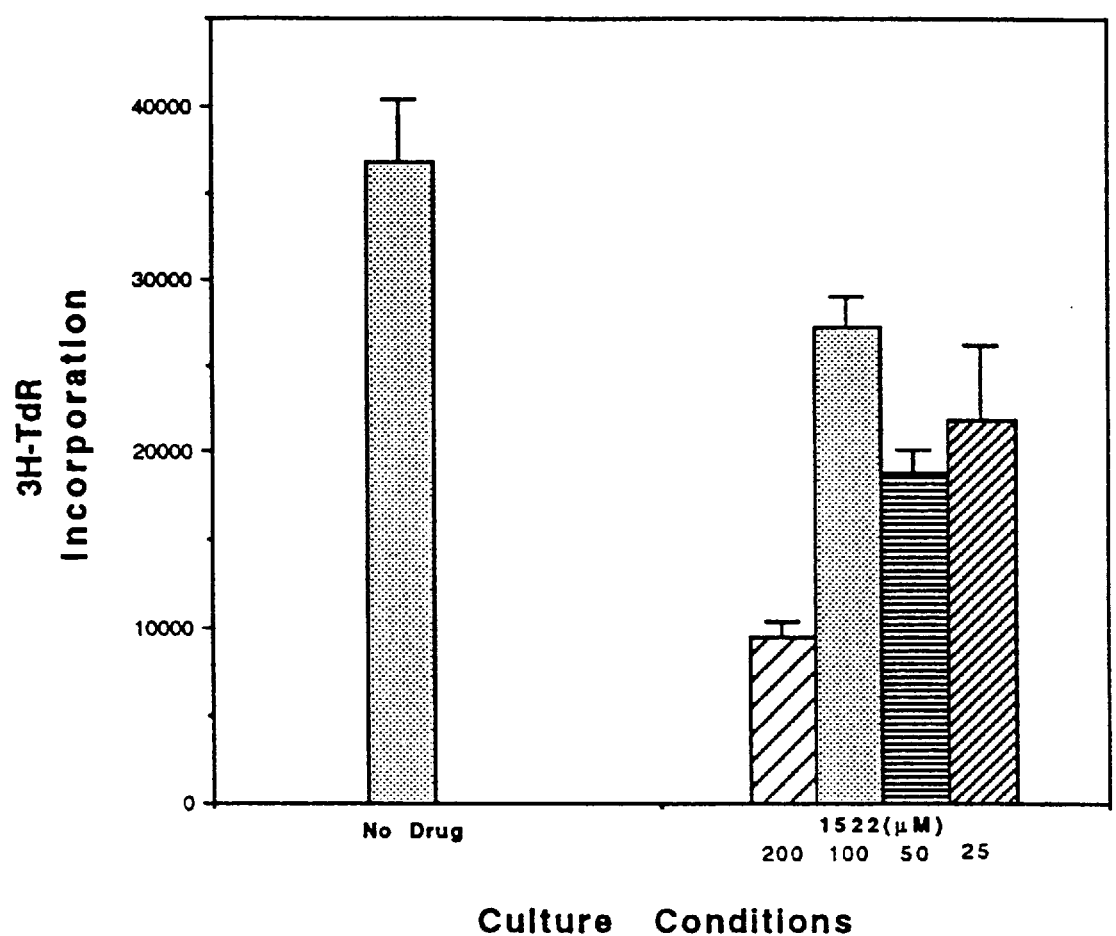
FIG. 3 shows the effects of inventive compound no. 1522 on inhibition of murine thymocyte proliferation stimulated by Concanavalin A (ConA) and interleukin-1 alpha (IL-1α).

This example shows the effects of inventive compound no. 1522 on inhibition of murine thymocyte proliferation stimulated by ConA and IL-1α. Compound no 1522 was added to the cells at the doses indicated two hours prior to activation with ConA and IL-1α. Compound no. 1522 inhibited thymocyte proliferation as is shown in FIG. 3. Background counts were less than 200 cpm.

EXAMPLE 13

Figure 4:
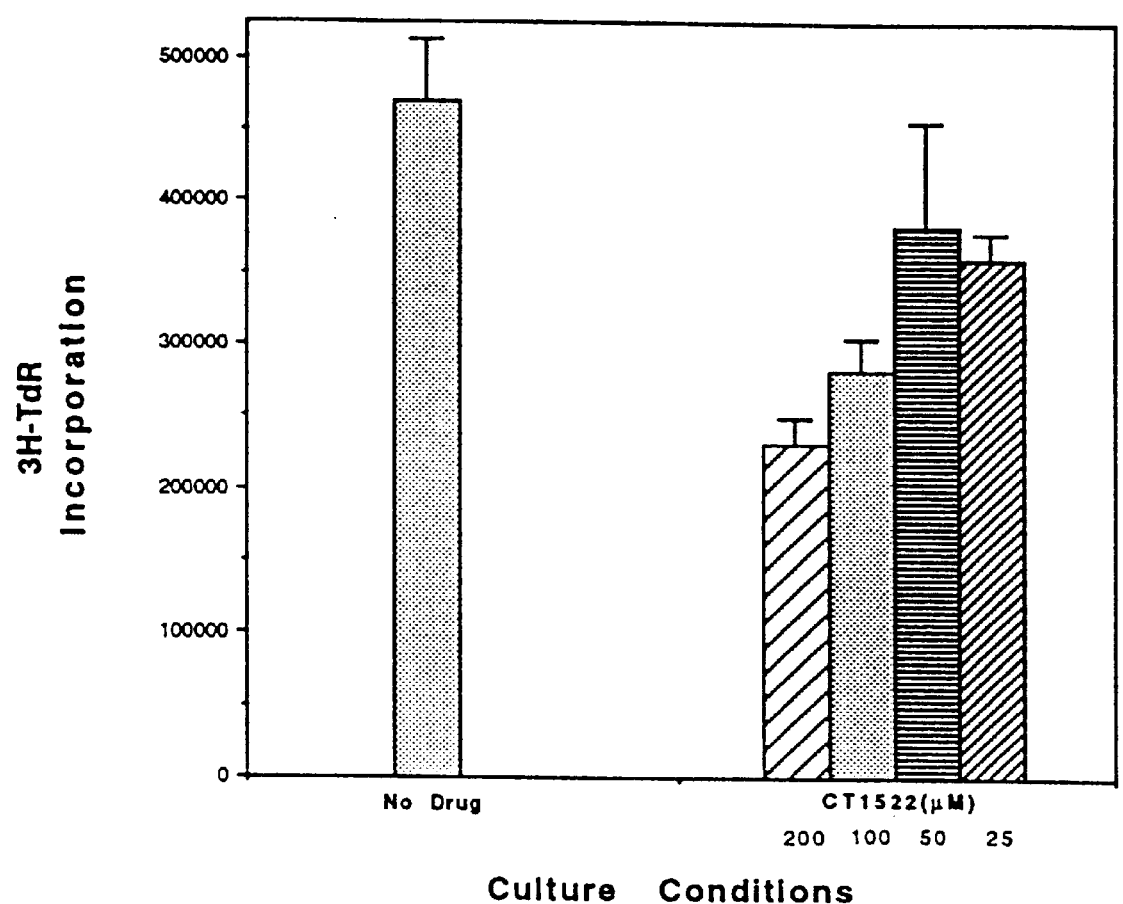
FIG. 4 shows the effects of inventive compound no. 1522 on inhibition of thymocyte proliferation stimulated by ConA and interleukin-2 (IL-2). Thymocyte proliferation was inhibited at the higher doses shown in FIG. 4.

This example shows the effects of inventive compound no. 1522 on inhibition of thymocyte proliferation stimulated by ConA and interleukin-2 (IL-2) (20 ng/ml). Compound no. 1522 was added to the cells two hours prior to activation with ConA and IL-2. As shown in FIG. 4, compound no. 1522 inhibited thymocyte proliferation at the higher doses tested.

EXAMPLE 14

Figure 5:
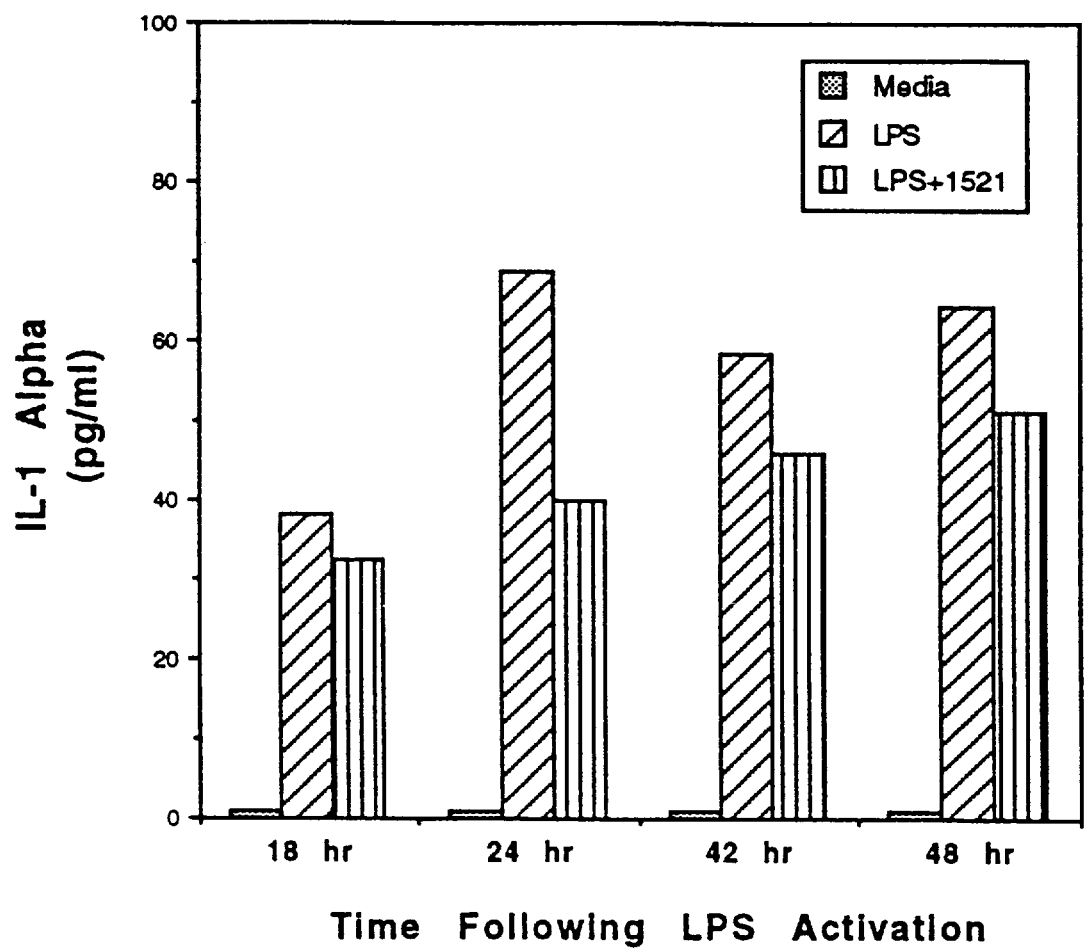
FIG. 5 illustrates the ability of inventive compound no. 1521 to inhibit IL-1α release from murine peritoneal macrophages when stimulated with LPS. This assay is a model for septic shock. As represented in FIG. 5, 1521 inhibited IL-1α release.

This example illustrates the ability of inventive compound no. 1521 to inhibit IL-1α release from murine peritoneal macrophages when stimulated with LPS. This assay is a model for septic shock. Macrophages ($10^5$) were treated with LPS at 10 μg/ml in RPMI media containing 10% fetal calf serum. Supernatants were assayed for IL-1α by an ELISA technique at various times following LPS stimulation. The cells were treated one hour prior to LPS stimulation with 0.25 mM 1521. As can be seen from the data reported in FIG. 5, compound no. 1521 inhibited IL-1α release.

EXAMPLE 15

Figure 6:
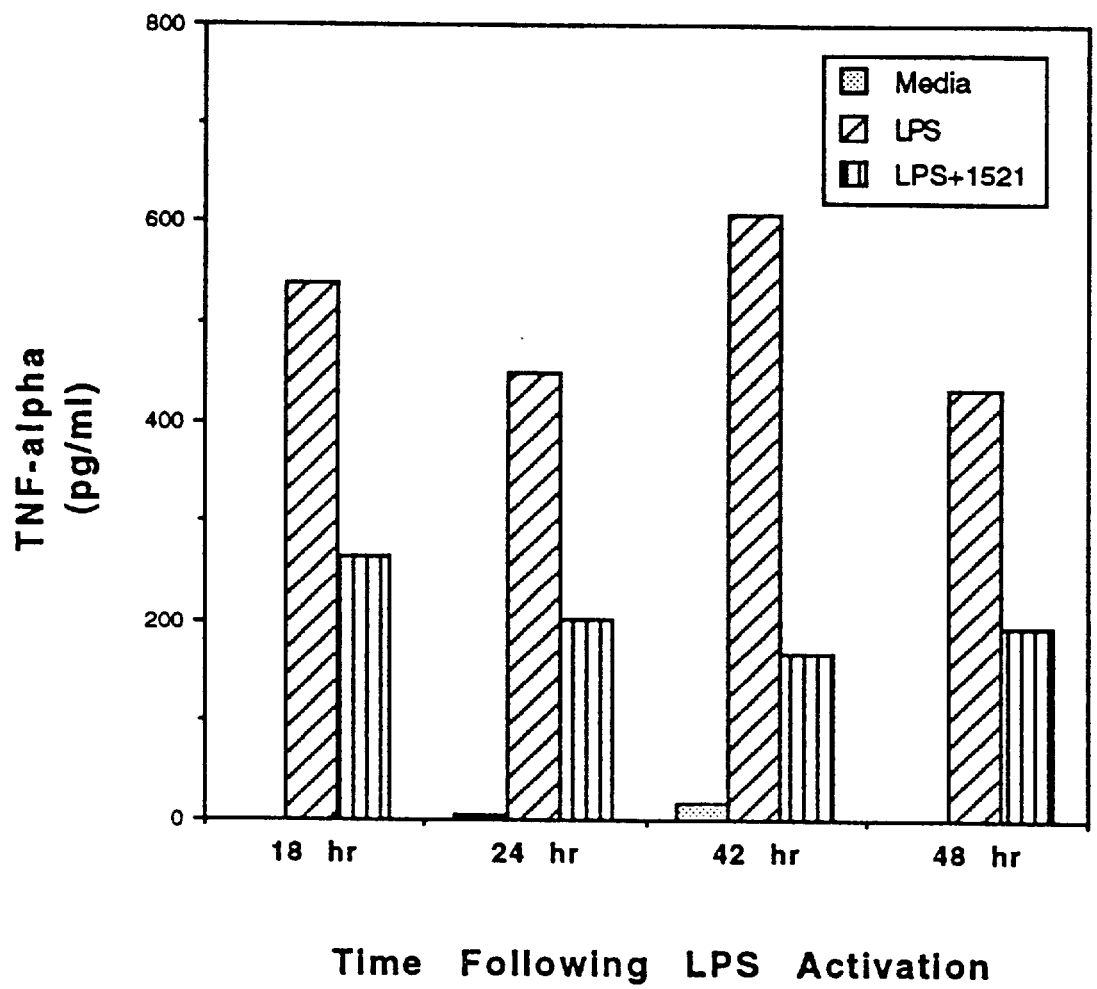
FIG. 6 illustrates inventive compound no. 1521's ability to inhibit TNF-α release from murine peritoneal macrophages when stimulated with LPS. This assay is a model for septic shock.

This example illustrates the ability of inventive compound no. 1521 to inhibit TNF-α release from murine peritoneal macrophages when stimulated with LPS. This assay is a model for septic shock. Macrophages ($10^5$) were treated with LPS at 10 μg/ml in RPMI media containing 10% fetal calf serum. Supernatants were assayed for TNF by an ELISA technique at various times following LPS stimulation. The cells were treated one hour prior to LPS stimulation with 0.25 mM of inventive compound no. 1521. As can be seen deduce from data reported in FIG. 6, compound no. 1521 inhibited TNF release.

EXAMPLE 16

Figure 7:
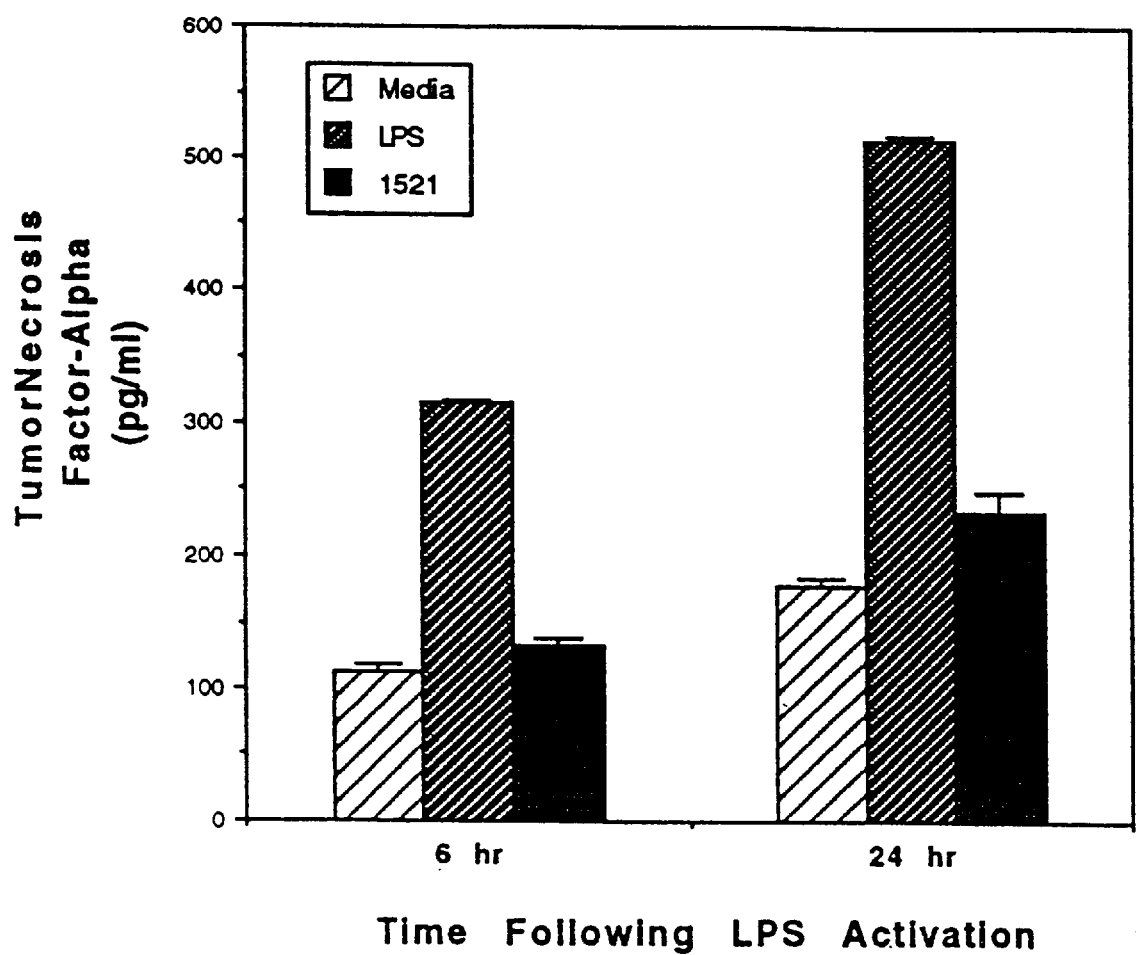
FIG. 7 illustrates the ability of inventive compound no. 1521 to inhibit TNF-α release from P388D1 cells (a murine monocyte/macrophage line) when stimulated with LPS.

This example illustrates the ability of compound no. 1521 to inhibit TNF-α release from P388D1 cells (a murine monocyte/macrophage line) when stimulated with LPS. This assay is a model for septic shock. P388D1 cells ($10^5$) were treated with LPS at 10 μg/ml in RPMI media containing 10% fetal calf serum. Supernatants were assayed for TNF by an ELISA technique at various times following LPS stimulation. The cells were treated one hour prior to LPS stimulation with 0.25 mM compound no. 1521. As can be seen from the data reported in FIG. 7, compound no. 1521 inhibited TNF release,

EXAMPLE 17

This example illustrates the ability of inventive compound no. 1521 to inhibit IL-1α release from P388D1 cells when stimulated with LPS. This assay is a model for septic shock. P388D1 cells ($10^5$) were treated with LPS at 10 μg/ml in RPMI media containing 10% fetal calf serum. Supernatants were assayed for IL-1α by an ELISA technique at various

Figure 8:
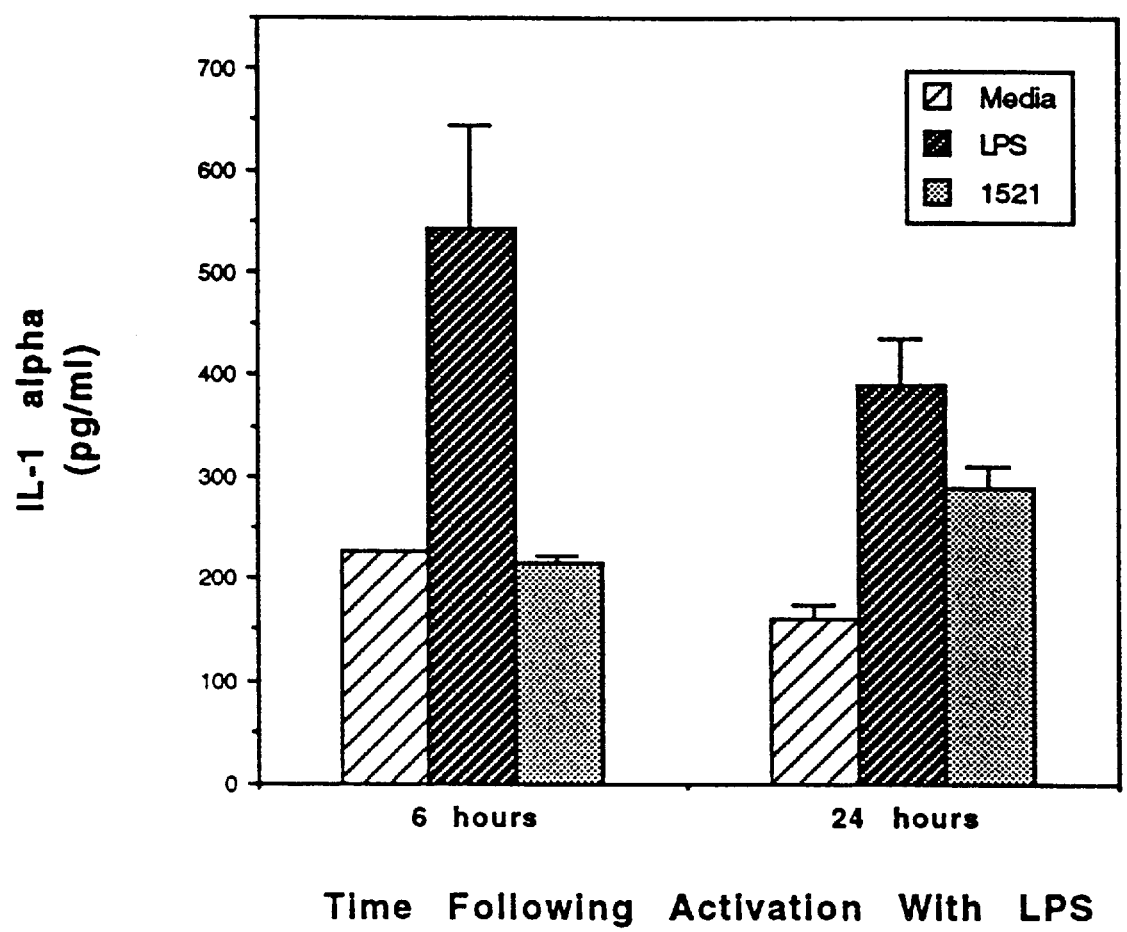
FIG. 8 reports data illustrating the ability of inventive compound no. 1521 to inhibit IL-1α release from P388D1 cells when stimulated with LPS. This assay is a model for septic shock. The data in FIG. 8 show inhibition of IL-1α release by compound no. 1521.

34 times following LPS stimulation. The cells were treated one hour prior to LPS stimulation with 0.25 mM of compound no. 1521. As can be deduced from data reported in FIG. 8, compound no. 1521 inhibited IL-1α release.

EXAMPLE 18

Figure 9:
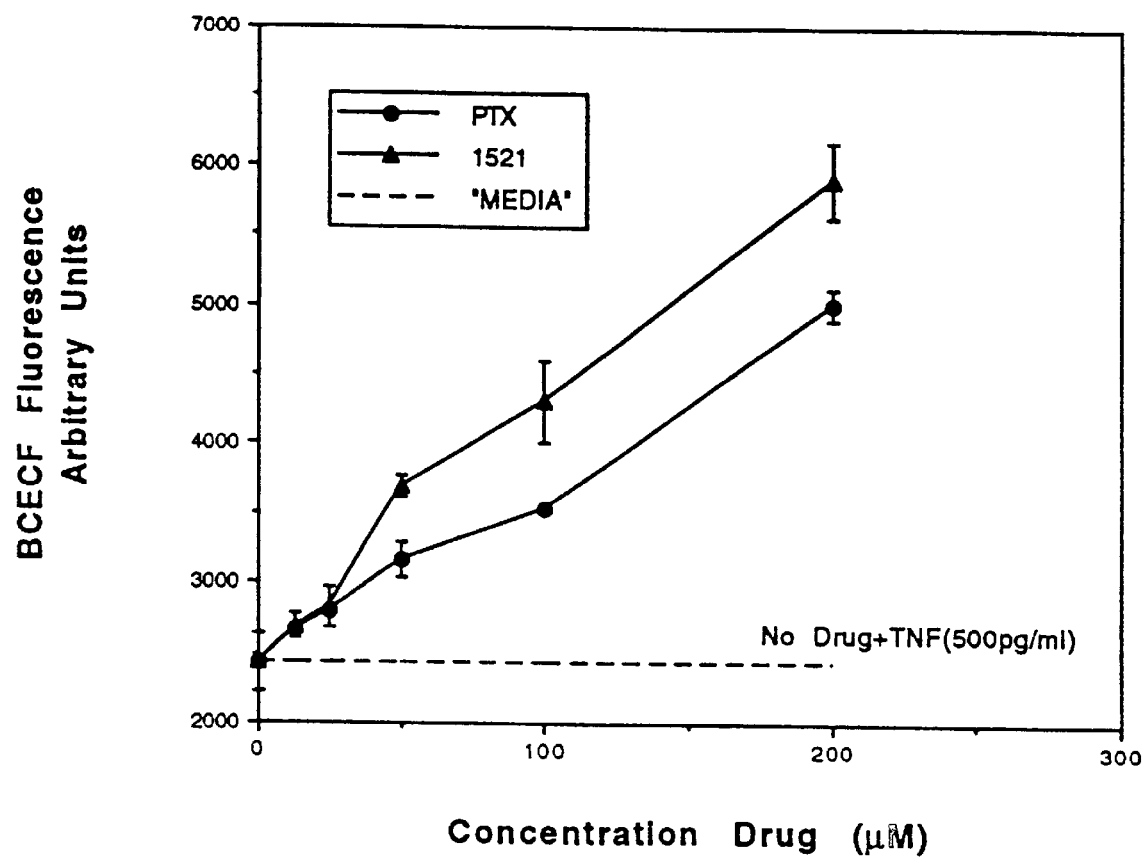
FIG. 9 reports data illustrating inventive compound no. 1521's ability to protect L929 cells (a murine fibroblast line) from the cytotoxic effects of TNF-α. This assay is a model for septic shock.

This example illustrates the ability of compound no. 1521 to protect L929 cells (a murine fibroblast line) from the cytotoxic effects of TNF-α. This assay is a model for septic shock. L929 cells ($10^5$) were treated with human TNF-α at 300 pg/ml in RPMI media containing 10% fetal calf serum with or without compound no. 1521 at the concentrations shown in FIG. 9. One day later, the cells were stained for viability using the fluorescent dye BCECF and fluorescence of the samples was analyzed using a Milipore plate reader. FIG. 9 shows that compound no. 1521 and comparative compound pentoxifylline (PTX) inhibited TNF-induced cytotoxicity in a dose dependent manner.

EXAMPLE 19

Figure 10:
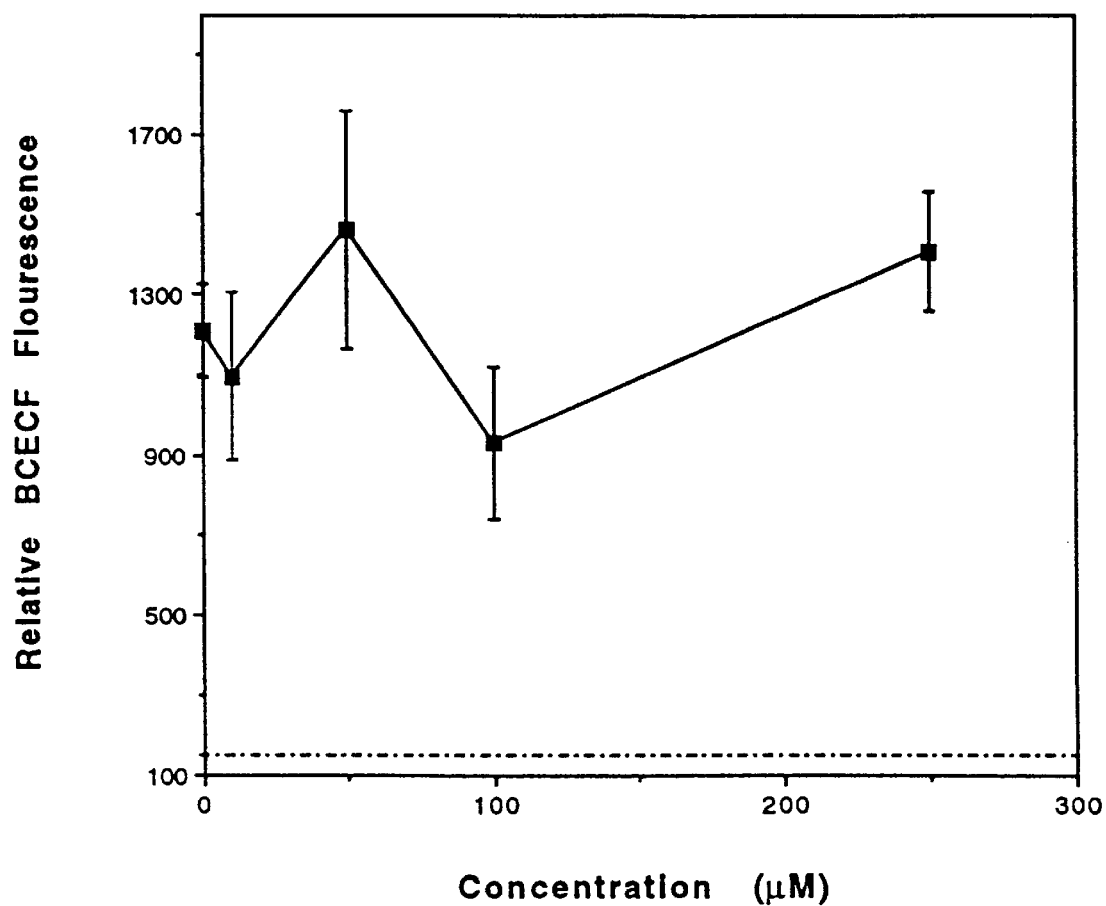
FIG. 10 shows the effect of inventive compound no. 1521 to inhibit adhesion of U937 cells to activated human umbilical vein endothelial cells (HUVEC). Background adhesion of U937 cells to non-activated HUVEC is shown as a dashed line.

This example shows the effect of inventive compound no. 1521 to inhibit adhesion of U937 cells to activated human umbilical vein endothelial cells (HUVEC). HUVEC cells were activated with 20 ng/ml of human TNF for 12 hours. Compound no. 1521 was added to samples one hour prior to adding TNF. U937 cells preloaded with a fluorescent dye were added to the HUVEC cells and adhesion measured after washing. Compound no. 1521 reduced adhesion. Background adhesion of U937 cells to non-activated HUVEC is shown as a dashed line. Assay results are reported in FIG. 10.

EXAMPLE 20

Figure 11:
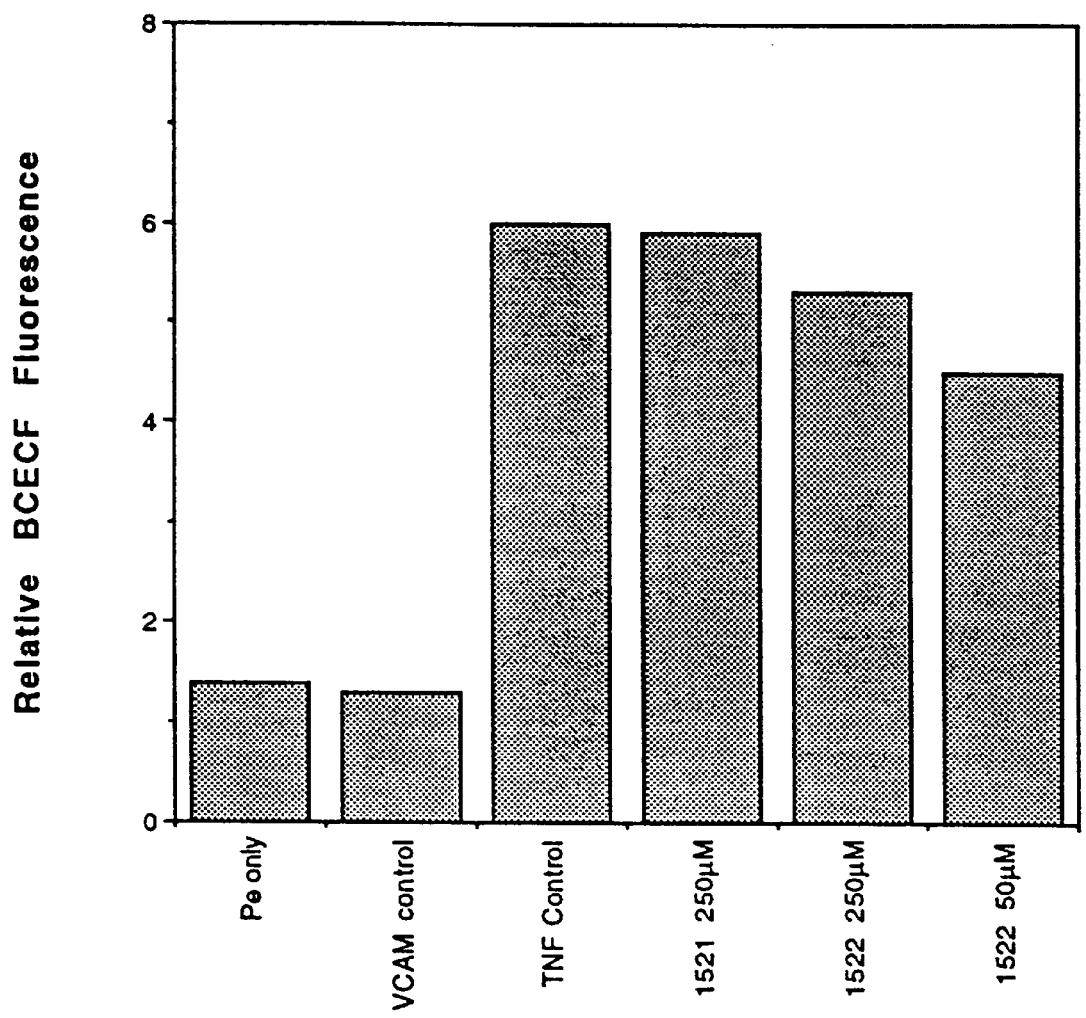
FIG. 11 shows the effects of inventive compounds nos. 1521 and 1522 to inhibit cell surface expression of VCAM in HUVEC cells.

This example shows the effects of inventive compounds nos. 1521 and 1522 to inhibit cell surface expression of VCAM in HUVEC cells. The cells were stimulated with human TNF-α (20 ng/ml) for 20 hours and then stained for immunofluorescence using a monoclonal antibody recognizing VCAM, followed by a goat anti-mouse antibody conjugated to phycoerythrin. The cells were analyzed for antibody binding using flow cytometry. FIG. 11 shows an analysis of mean fluorescence intensity of cells analyzed by flow cytometry for compounds nos. 1521 and 1522 at the indicated drug concentrations.

EXAMPLE 21

Figure 12:
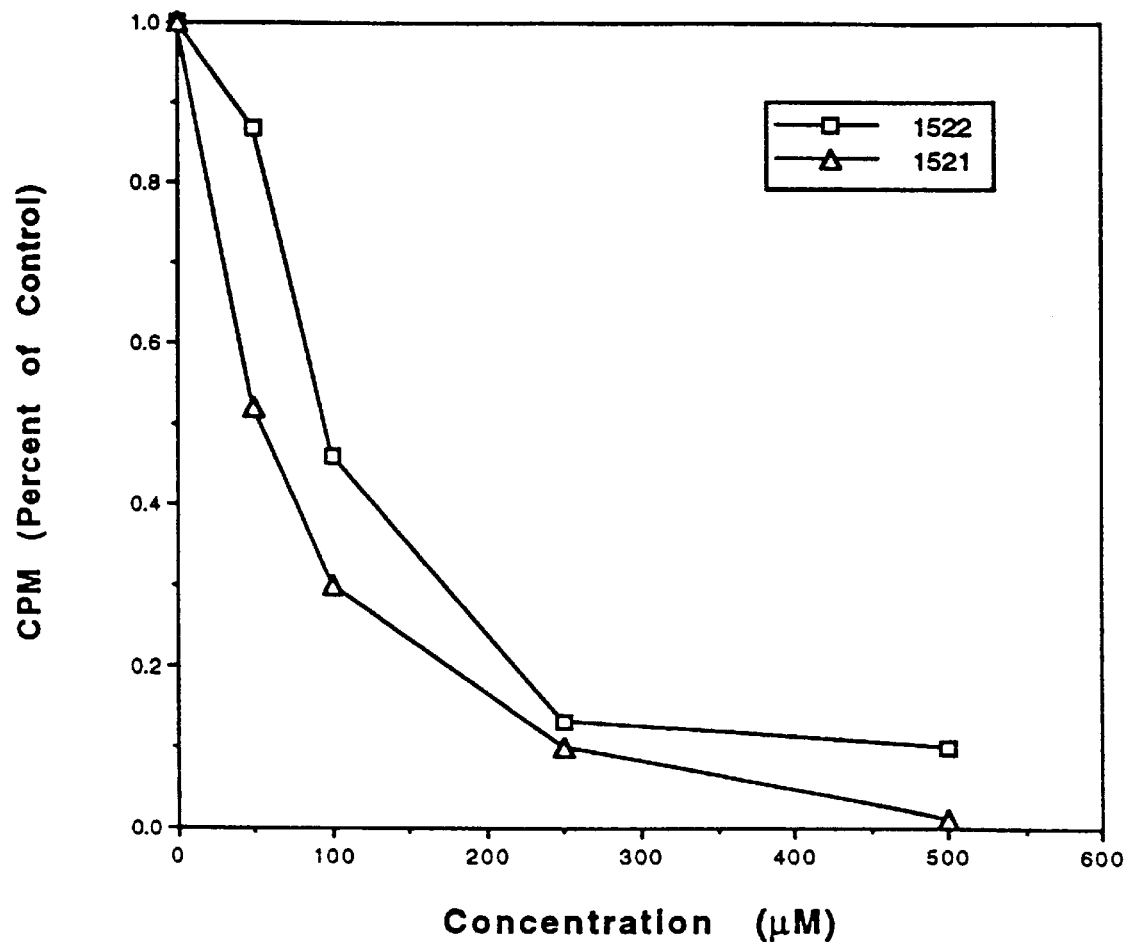
FIG. 12 illustrates data reporting inventive compounds nos. 1521 and 1522's ability to strongly inhibit proliferation of human stromal cells when stimulated with PDGF. This assay is a model for restenosis and treatment of atherosclerosis and coronary artery disease. Background counts (i.e., starved cells) were approximately 1% of control levels.

This example illustrates the ability of inventive compounds nos. 1521 and 1522 to strongly inhibit proliferation of human stromal cells when stimulated with PDGF. This assay is a model for restenosis and treatment of atherosclerosis and coronary artery disease. Stromal cells were starved in serum-free media for one day and then stimulated with 50 ng/ml PDGF-BB. The drugs were added at the indicated concentrations one hour prior to PDGF stimulation. Tritiated thymidine was added for one day at the time of PDGF stimulation and the cells were harvested and counted by liquid scintillation counting 24 hours later. Background counts (i.e., starved cells) were approximately 1% of control levels. FIG. 12 reports data showing that both compounds nos. 1521 and 1522 were active in this predictive in vitro model.

EXAMPLE 22

Figure 13:
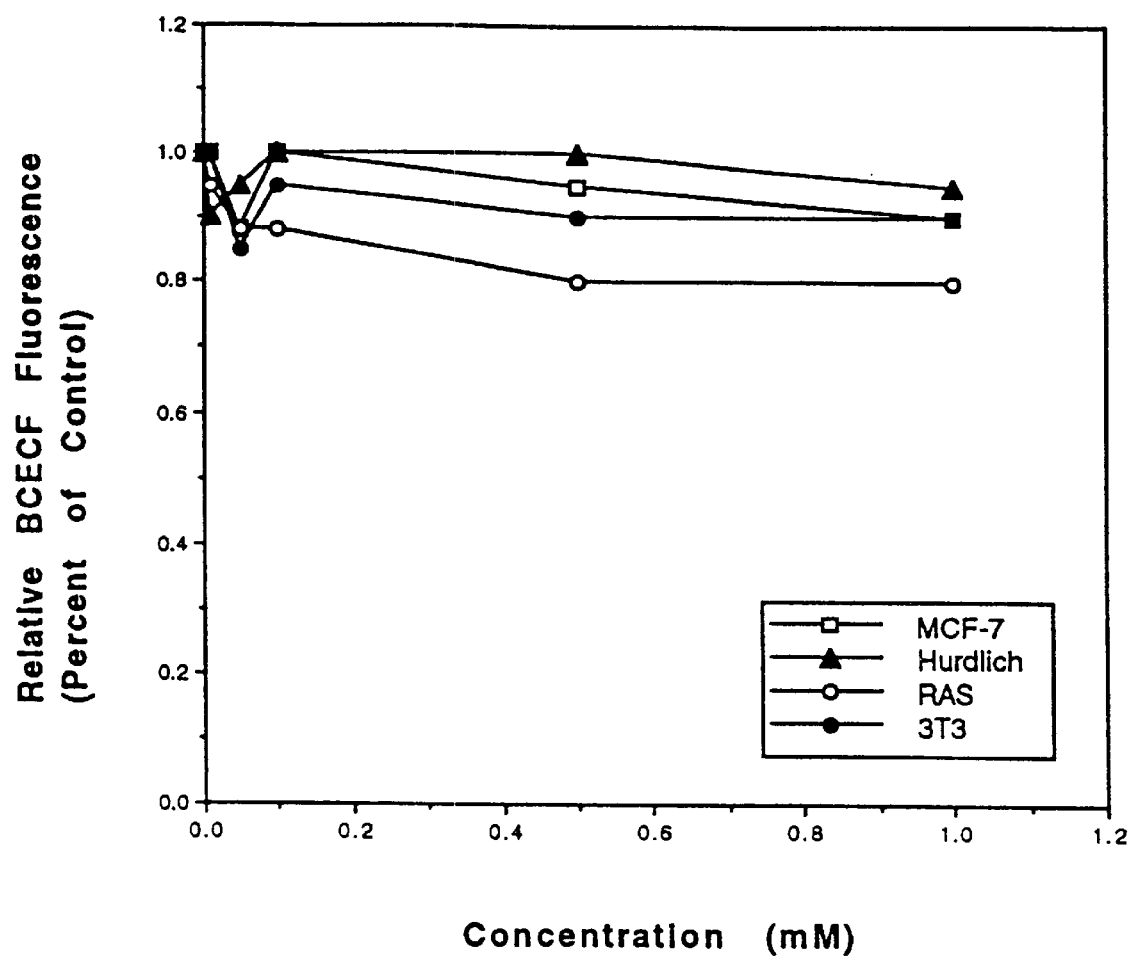
FIG. 13 reports cytotoxicity of inventive compound no. 1522 on several cell lines. The cells lines used were MCF-7 a human breast cancer-derived line, Hurdlich cells a human stromal derived line, RAS a codon-12 transformed malignant murine line, and NIH-3T3 a non-Ras transformed parent line of RAS.

This example shows that inventive compound no. 1522 is not cytotoxic to several cell lines. The cells lines used were MCF-7 a human breast cancer-derived line, Hurdlich cells a human stromal derived line, RAS a codon-12 transformed malignant murine line, and NIH-3T3 a non-Ras transformed parent line of RAS. The cells were treated with various concentrations of drug, and 24 hours later, stained for viability using BCECF and analyzed for fluorescent die uptake (indicating viable cells) using a fluorescence plate reader. As shown in FIG. 13, compound no. 1522 was non-toxic at therapeutic concentrations to the cells tested.

EXAMPLE 23

Figure 14:
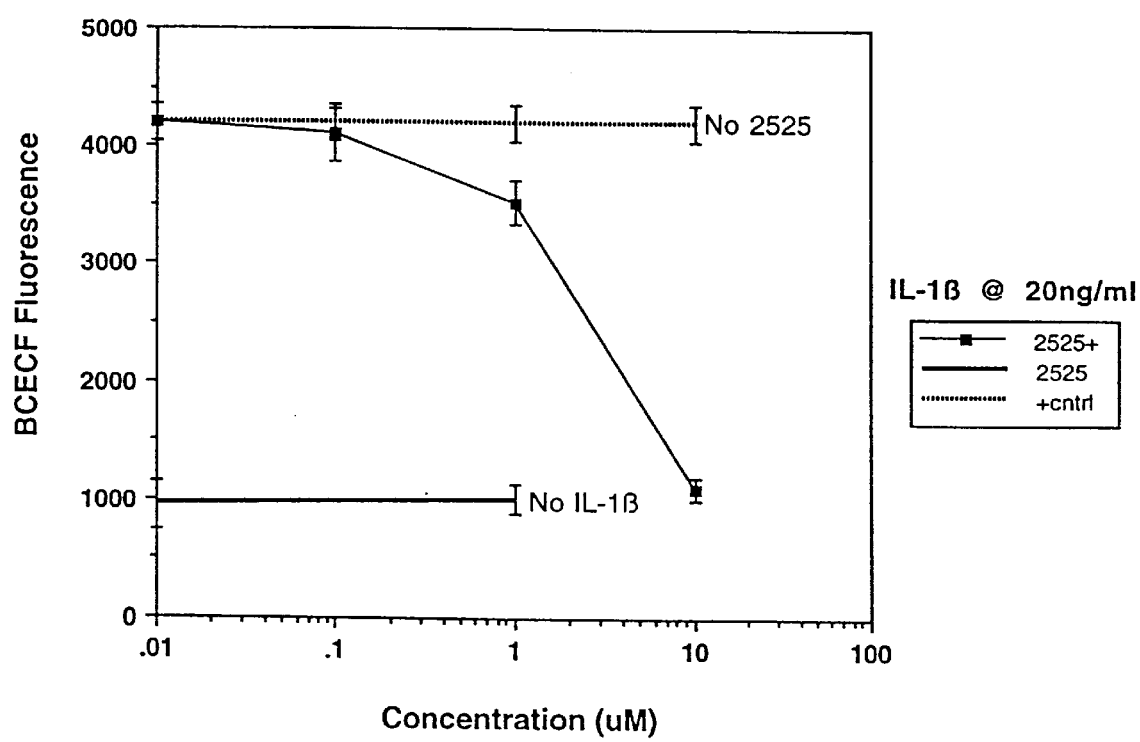
FIG. 14 reports data obtained in an assay measuring an ability of inventive compound no. 2525 to inhibit THP-1 cell adhesion to IL-1β-activated HUVEC.

This example illustrates inhibitive activity of inventive compound no. 2525 on THP-1 cell adhesion to IL-1β-activated HUVEC. In an investigative assay, HUVEC were stimulated with IL-1β (10 ng/ml), both in the absence and presence of varying concentrations of inventive compound for 8 hours in a 96-well microtiter plate. In the wellplate, human monocytic leukemia cell line THP-1 cells were added at 50,000 cells per well. The THP-1 cells were pre-incubated with BCECF, a fluorescence dye that can be use to measure cell number using a fluorescence plate reader. After 10 minutes at 37° C., the microtiter plate was inverted and spun at 900 rpm. The remaining adhering THP-1 cells were then analyzed. As shown in FIG. 14, non-stimulated background adherence was approximately 1000 relative units, increasing to approximately 4250 under IL-1β stimulation. The inventive compound no. 2525, as tested, significantly inhibited THP-1 adhesion, even at low concentratations between 1.0 and 10 $\mu$M.

EXAMPLE 24

Figure 15:
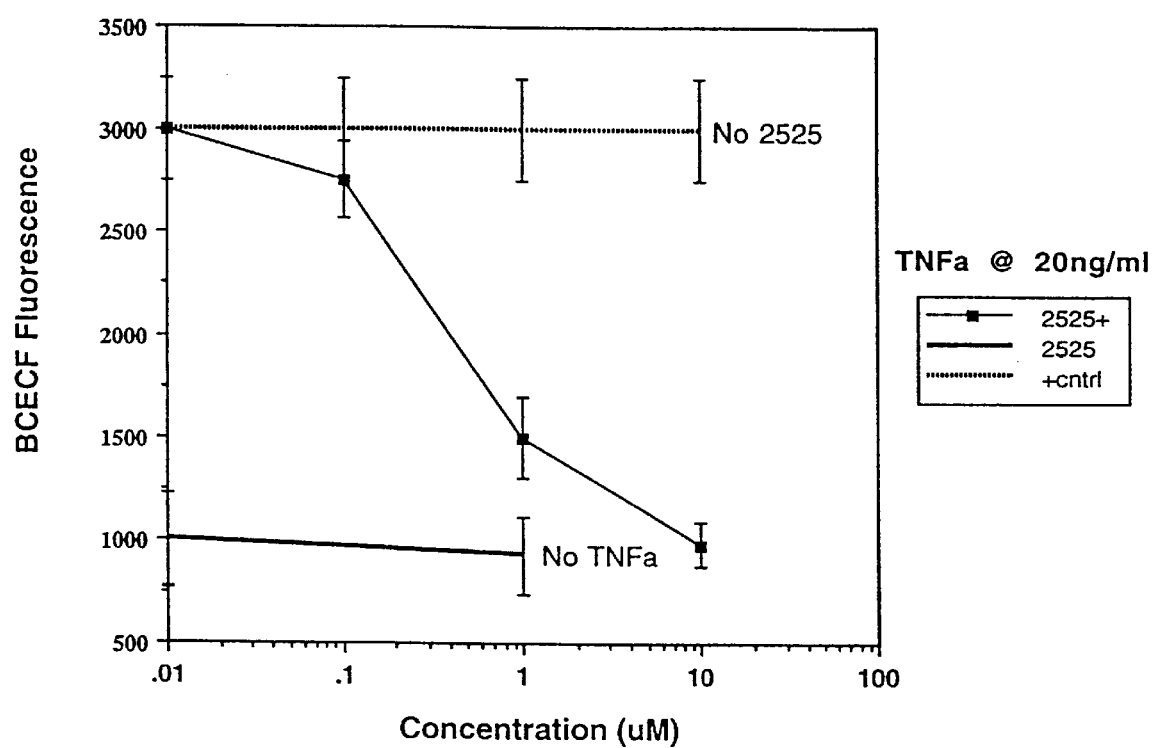
FIG. 15 illustrates data obtained in a THP-1 (TNFα-activated HUVEC) adhesion investigative protocol with inventive compound no. 2525.

This example illustrates inhibitive activity of inventive compound no. 2525 on THP-1 cell adhesion to TNFα-activated HUVEC. In an investigative assay, representative of the protocol employed in Example 23, HUVEC were stimulated with TNF α instead of IL-1β. As shown by results reported in FIG. 15, non-stimulated background adherence was approximately 1000 relative units, increasing to approximately 3000 under TNF stimulation. The inventive compound 2525, representative of compounds disclosed herein, significantly inhibited THP-1 adhesion at concentrations ranging from 0.1 to 10 $\mu$M, representative of anticipated in vivo therapeutic concentrations.

EXAMPLE 25

Figure 16:
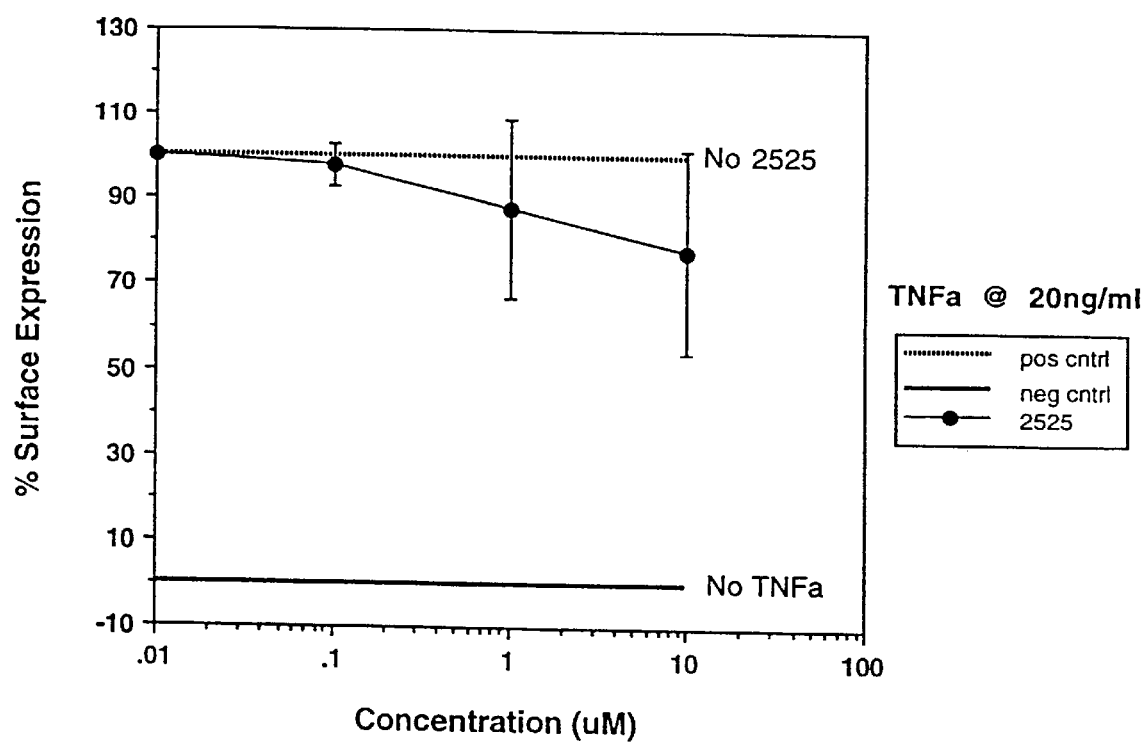
FIG. 16 reports data obtained for inventive compound no. 2525, showing inhibition of ICAM surface expression in HUVEC cells stimulated with TNF-α by compound no. 2525.

This example shows the effect of inventive compound no. 2525 to inhibit cell surface expression of ICAM in HUVEC cells. The cells were stimulated with human TNF-α (20 ng/ml) for 20 hours and then stained for immunofluorescence using a monoclonal antibody recognizing ICAM, followed by a goat anti-mouse antibody conjugated to phycoerythrin. The cells were analyzed for antibody binding using flow cytometry. FIG. 16 reports % surface expression, determined by analysis of mean fluorescence intensity of cells analyzed by flow cytometry, for compound no. 2525, at concentration shown. As reported, compound no. 2525, represented of the inventive compounds disclosed herein, inhibited ICAM surface expression.

EXAMPLE 26

Figure 17:
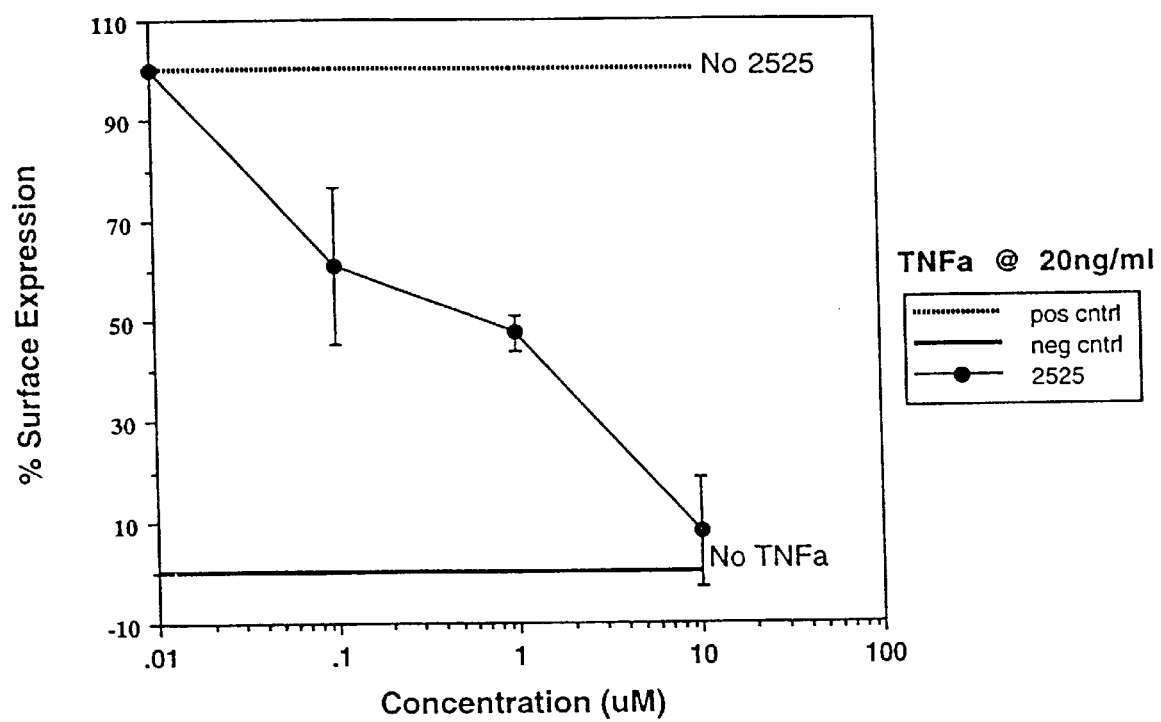
FIG. 17 is a plot of percent surface expression versus concentration of compound no. 2525 in a vascular cell adhesion molecule (VCAM) expression on HUVEC assay used to determine an ability of the inventive compounds to inhibit surface expression of VCAM.

This example was used to investigate inhibition of vascular cell adhesion molecule (VCAM) expression on HUVEC by inventive compound no. 2525. VCAM expression by endothelial cells is an early event in atherogenesis and multiple sclerosis, among other various autoimmune diseases. Results obtained in a protocol similar to that employed in Example 20, are reported in FIG. 17. FIG. 17, a plot of percent surface expression versus concentration of compound no. 2525, illustrates that the inventive compound tested is able to inhibit surface expression of VCAM in a HUVEC cell stimulate by TNF-α.

EXAMPLE 27

This example provides data used in preparing a dose response curve used to generate 50% inhibition concentrations (IC50) of for inventive compound no. 2514 for murine thymocyte proliferation, co-stimulated by Concanavalin A (ConA) and interleukin-2 alpha (IL-2). ConA along with IL-2 co-stimulation, induces T-cell proliferation and differentiation.

Figure 18:
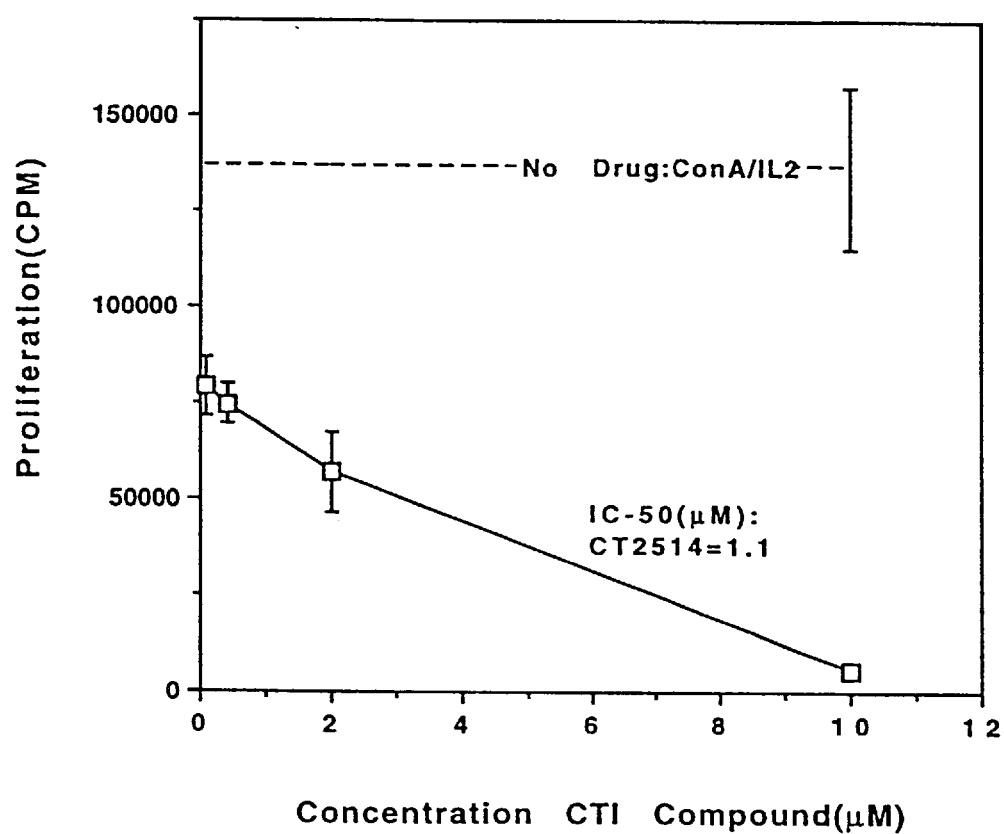
FIG. 18 is a dose response curve used to generate 50% inhibition concentrations (IC50) for inventive compound no. 2514 on murine thymocyte proliferation.
Figure 19:
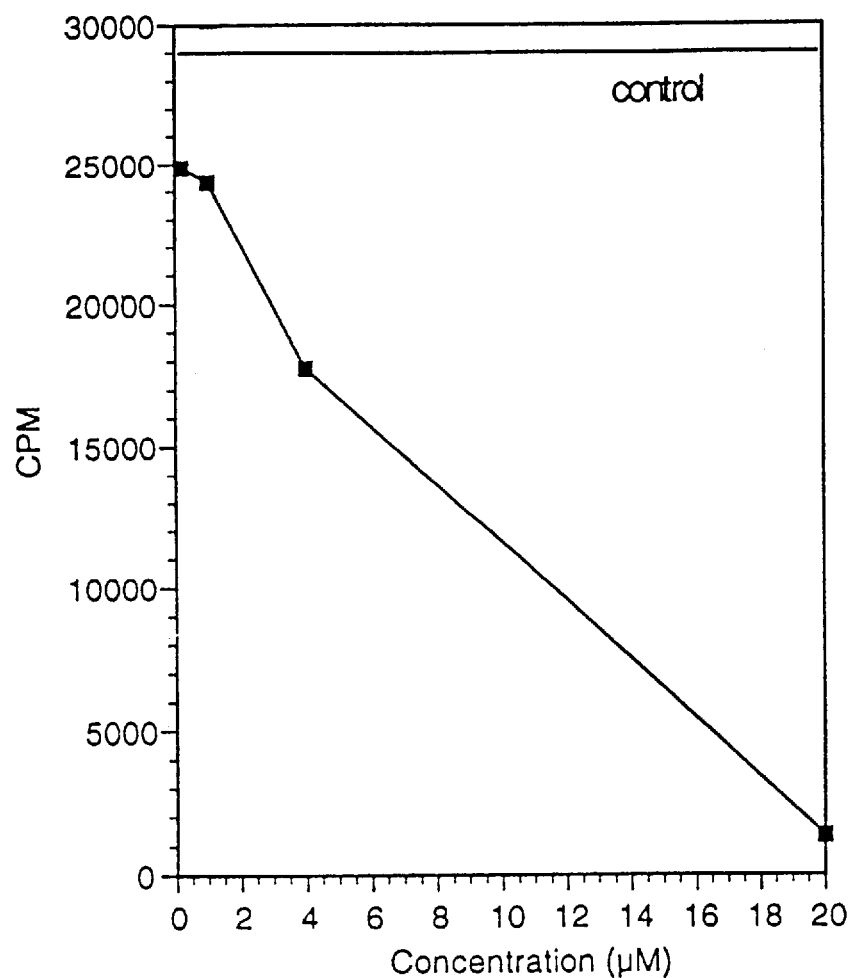
FIG. 19 reports data obtained in an investigative protocol used to determine inhibitive characteristics of inventive compound no. 2514 in a mixed lymphocyte reaction.

Thymuses, obtained from normal, female Balb/C mice, were dissociated and plated into 96-well plates at a density of $2\times10^5$ cells/well. ConA (0.25 mg/ml) and IL-2 (15 U/ml) were added to the wells. The cells were incubated for 4 days at 37° C. On day 4, the cells were pulsed with tritiated thymidine and incubated for an additional 4 hours. The amount of tritiated thymidine dye incorporated by the harvested cells was determined in a liquid scintillation counter. Drug doses (reported in FIG. 18) were added two hours prior to ConA and IL-2 activation. Background counts were less than 200 cpm. The inventive compound tested, representative of the inventive compounds disclosed herein, inhibit thymocyte proliferation and activation.

EXAMPLE 28

This example illustrates the ability of the inventive compounds to inhibit a proliferative response of lymphocytes in a mixed lymphocyte reaction of inventive compound no. 2514 using a protocol similar to that disclosed above and employed in example 10. The mixed lymphocyte reaction shows a proliferative response of PBMC (peripheral blood mononuclear cells) to allogeneic stimulation determined in a two-way mixed lymphocyte reaction. Assay results are reported in FIG. 18. The inventive compound tested, representative of the inventive compounds disclosed herein, showed activity in this immune modulating activity assay procedure.

What is claimed is:

1. A compound, or a hydrate, salt, or solvate of the compound, having the formula:

$$\text{CORE MOIETY}-(R)_j$$

wherein:

j is an integer from one to three;

the core moiety has from one to three, five- to six-membered ring structures in a predominantly planar configuration, having at least one nitrogen, wherein R is bound to the nitrogen; and R is independently selected from the group consisting of hydrogen, halogen, hydroxyl, amino, $C_{(1-10)}$ alkyl, $C_{(2-10)}$ alkenyl, and formula I; wherein at least one R is formula I $$-(CH_2)_n-C-(R_1)_p \qquad I$$

wherein:

n is an integer from three to twenty;

p is three;

$R_1$ is independently selected from the group consisting of hydrogen, halogen, hydroxide, $C_{(1-10)}$ alkyl, $C_{(1-10)}$ ether, C$_{(2-10)}$ alkenyl, =N—O$_2$, wherein R$_2$ is selected from the group consisting of hydrogen, C$_{(1-10)}$ alkyl, C$_{(2-10)}$ alkenyl, and —(CH2)$_s$C(R$_3$)$_t$, wherein s is zero or an integer from one to ten, wherein t is three, wherein R$_3$ is selected from the group consisting of hydrogen, halogen, hydroxide, C$_{(1-10)}$ alkyl, C$_{(1-10)}$ alkoxy, C$_{(2-10)}$ alkenyl, and =N—OR$_2$, at least one R$_1$ or one R$_3$ is =N—OR$_2$, p or t corresponding to the at least one R$_1$ or one R$_3$ instead being two; and, a second R$_1$ or second R$_3$, bonded to the same —C as the at least one R$_1$ or one R$_3$, is other than =N—OR$_2$, with the proviso that if the core moiety is a xanthine, n is an integer not less than five.

2. The compound according to claim 1, wherein at least one of (CH$_2$)$_n$ or (CH$_2$)$_s$ has two or four carbon atoms being unsaturated and represented instead by —CH=CH— or is interrupted by at least one oxygen atom.

3. The compound according to claim 2, wherein the —CH=CH— is in a cis configuration.

4. The compound according to claim 1, wherein one R$_1$ of —C(R$_1$)$_2$ is =N—OR$_2$, R$_2$ is selected from the group consisting of hydrogen and C$_{(1-10)}$ alkyl, and the second R$_1$ is selected from a C$_{(1-10)}$ alkyl or C$_{(1-10)}$ alkoxy.

5. The compound according to claim 1, wherein one R$_1$ is =N—OR$_2$, and a second R$_1$, bonded to the same —C as the one R$_1$ is other than =N—OR$_2$.

6. The compound according to claim 1, wherein one R$_3$, is =N—OR$_2$, and a second R$_3$, bonded to the same —C as the one R$_3$, is other than =N—OR$_2$.

7. The compound according to claim 1, wherein n is an integer from about three to about eighteen.

8. The compound according to claim 1, wherein n is an integer from about three to about seven.

9. The compound according to claim 1, wherein one R$_1$ of —C(R$_1$)$_2$ is =N—OR$_2$, R$_2$ being hydrogen or C$_{(1-10)}$ alkyl, and the second R$_1$ is a C$_{(1-10)}$ alkyl or C$_{(1-10)}$ alkoxy.

10. The compound according to claim 1, wherein when R, R$_1$, R$_2$ or R$_3$ is a substituted C$_{(1-10)}$ alkyl, C$_{(1-10)}$ alkoxy, C$_{(2-10)}$ alkenyl, cyclic or heterocyclic groups, corresponding substituents are selected from the group consisting of amide, primary, secondary and tertiary amine, C$_{(2-8)}$ alkenyl, C$_{(1-8)}$ alkyl, C$_{(1-8)}$ alkoxy, azide, carbonate, carbonyl, carboxylic acid, cyanide, C$_{(1-8)}$ haloalkyl, isocyanate, isothiocyanate, phosphate, phosphonate, primary, secondary or tertiary alcohol, sulfonate, sulfone, sulfoxide, thioamide, thiocarbonate, thioester, thiolester, thiol, thiourea and urea.

11. The compound according to claim 10, wherein the haloalkyl is a mono-, di- or tri-haloalkyl.

12. The compound according to claim 10, wherein the alcohol is selected from the group consisting of diol, methanol, butanol, 1-cyclopentanol, ethanol, 2-ethyl-3-methyl-1-propanol, pentanol, propanol, and methylcyclohexanol.

13. The compound according to claim 1, wherein the core moiety is selected from the group consisting of substituted or unsubstituted barbituric acid; benzamide; lactam; glutarimide; homophthalimide; hydrophthalimide; imidazole; imidazole amide; indomethacin; isocarbostyril; lumazine; N-alkylheterocyclic; N-heterocyclic; pteridine; pthalimide; piperidine; pyridine; pyrimidine; pyrrole amide; quaternized N-heterocyclic; quinolizinedione; quinazolinone; quinolone; recorsinol; succinimide; theobromine; thymine; triazine; uric acid; uracil; vitamins A, E or K; or xanthine.

14. The compound according to claim 1, wherein the core moiety is selected from the group consisting of substituted or unsubstituted glutarimide, methylthymine, methyluracil, thymine, theobromine, uracil and xanthine.

15. The compound according to claim 1, wherein the core moiety is selected from the group consisting of: 1,3-cyclohexanedione, 1,3-cyclopentanedione; 1,3-dihydroxynaphthalene; 1-methyllumazine; methylbarbituric acid; 3,3-dimethylglutarimide; orotic acid; tetra or hexahydrophthalimide; orthophenol; prostacyclin; 2-hydroxypyridine; methyldihydroxypyrazolopyrimidine, specifically, 1,3-dimethyldihydroxypyrazolo[4,3-d]pyrimidine; methylpyrrolopyrimidine; 1-methylpyrrolo[2,3-d]pyrimidine; 1,3-dihydroxynapthalene; 1-pyrrole amides; 2-pyrrole amides; 3-pyrrole amides; 1,2,3,4-tetrahydroisoquinolone; 1-methyl-2,4(1H,3H)-quinolizinedione; quinazolin-4(3H)-one; sulindac; dihydrothymine; alkyl-substituted C$_{(1-6)}$ thymine; 2,4-dioxohexahydro-1.3.5tetrazine; methylthymine; alkyl-substituted C$_{(1-6)}$ uracil; uracil fused to naphthalene; 6-aminouracil; 1-methyl-5,6-dihydrouracil; 1-methyluracil; 5- and/or 6-position substituted uracil; B-ionone as vitamin A; 2,6,6-methyl-1-cyclohexene-1-acetaldehyde as vitamin A; tetralone to vitamin K; 1,7-dimethylxanthine, 3,7-dimethylxanthine; 3-methylxanthine; 3-methyl-7-methylpivaloylxanthine; 8-substituted xanthines, having substituents N or S; and 7-methylhypoxanthine.

16. The compound according to claim 1, wherein the core moiety is xanthine, the at least one R having formula I is bonded to an N$_1$ xanthine nitrogen and N$_3$ and N$_7$ xanthine nitrogens are independently substituted by a member selected from the group consisting of hydrogen, methyl, fluoro, chloro and amino.

17. The compound according to claim 1, wherein R is bonded to a nitrogen of the core moiety.

18. The compound according to claim 1, wherein the compound has the following formula II

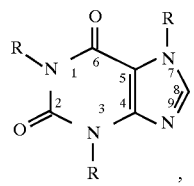

wherein

R is defined as in claim 1.

19. The compound according to claim 18, wherein one R$_1$ of —C(R$_1$)$_2$ is =N—OR$_2$, R$_2$ is hydrogen or methyl and a second R$_1$ is a C$_{(1-10)}$ alkyl or C$_{(1-10)}$ alkoxy.

20. The compound according to claim 1, wherein the compound is selected from the group consisting of:

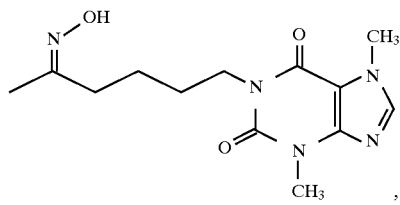
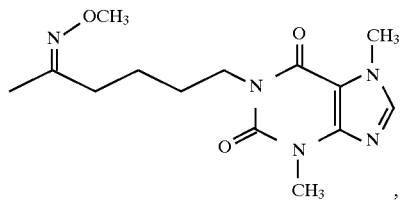
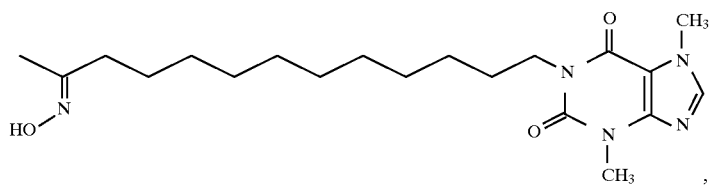
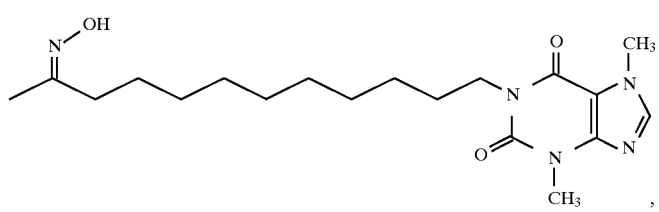
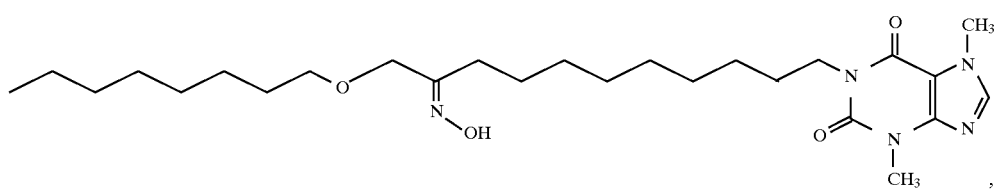
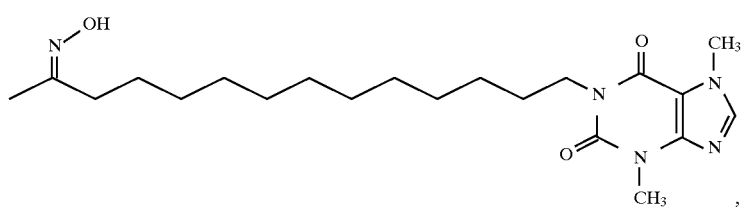
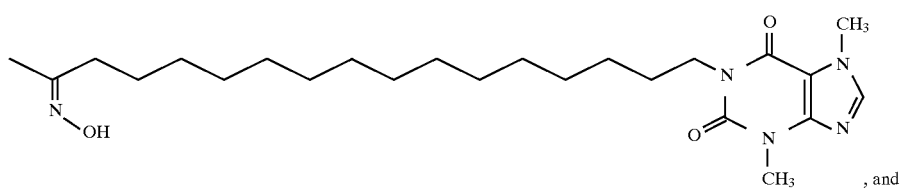
, and
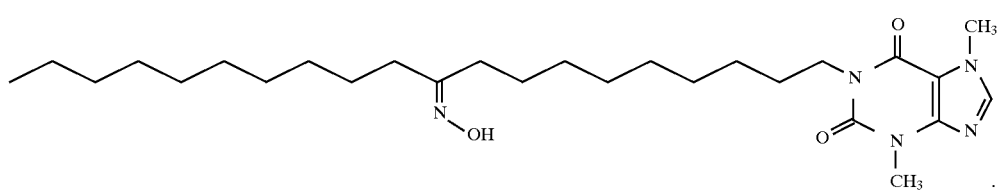
21. A pharmaceutical composition comprising a compound of claim 1 in admixture with a pharmaceutically acceptable excipient or carrier.
22. A pharmaceutical composition comprising a compound having a formula II

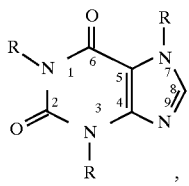

wherein:

R is independently selected from the group consisting of hydrogen, halogen, hydroxyl, amino, $C_{(1-10)}$ alkyl, $C_{(2-10)}$ alkenyl, and formula I, wherein at least one R is formula I;

$$—(CH_2)_n—C—(R_1)_p \quad \text{I}$$

wherein:

n is an integer from five to twenty;

p is two or three;

$R_1$ is independently selected from the group consisting of hydrogen, halogen, hydroxide, $C_{(1-10)}$ alkyl, $C_{(1-10)}$ ether, $C_{(2-10)}$ alkenyl, and $=N—OR_2$, wherein $R_2$ is selected from the group consisting of hydrogen $C_{(1-10)}$ alkyl, $C_{(2-10)}$ alkenyl, and $—(CH_2)_s—C(R_3)_t$, wherein s is zero or an integer frown one to ten, wherein t is an integer two or three, wherein $R_3$ is selected from the group consisting of hydrogen, halogen, hydroxide, $C_{(1-10)}$ alkyl, $C_{(1-10)}$ alkoxy, $C_{(2-10)}$ alkenyl, and $=N—OR_2$, at least one $R_1$ or one $R_3$ is $=N—OR_2$, p or t corresponding to the at least one $R_1$ or one $R_3$ being two; and, a second $R_1$ or second $R_3$, bonded to the same —C as the at least one $R_1$ or one $R_3$, is other than $=N—OR_2$.

* * * * *